United States Patent
Shankar et al.

(10) Patent No.: US 12,307,303 B2
(45) Date of Patent: May 20, 2025

(54) CLOUD EDGE DEVICE VIRTUALIZATION

(71) Applicant: Oracle International Corporation, Redwood Shores, CA (US)

(72) Inventors: Alok Shankar, San Jose, CA (US); Zachary Simpson Mayer, Seattle, WA (US)

(73) Assignee: Oracle International Corporation, Redwood Shores, CA (US)

( * ) Notice: Subject to any disclaimer, the term of this patent is extended or adjusted under 35 U.S.C. 154(b) by 772 days.

(21) Appl. No.: 17/529,546

(22) Filed: Nov. 18, 2021

(65) Prior Publication Data

US 2022/0327003 A1 Oct. 13, 2022

Related U.S. Application Data

(60) Provisional application No. 63/173,244, filed on Apr. 9, 2021.

(51) Int. Cl.
| | |
|---|---|
| *G06F 9/50* | (2006.01) |
| *G06F 9/455* | (2018.01) |
| *G06F 11/34* | (2006.01) |
| *H04L 41/50* | (2022.01) |

(52) U.S. Cl.
CPC .......... *G06F 9/5077* (2013.01); *G06F 9/455* (2013.01); *G06F 9/5005* (2013.01); *G06F 11/3409* (2013.01); *G06F 11/3414* (2013.01); *G06F 11/3433* (2013.01); *G06F 11/3457* (2013.01); *G06F 2009/45562* (2013.01); *G06F 2009/45587* (2013.01); *H04L 41/50* (2013.01)

(58) Field of Classification Search
None
See application file for complete search history.

(56) References Cited

U.S. PATENT DOCUMENTS

| | | | |
|---|---|---|---|
| 2020/0228602 A1* | 7/2020 | Spoczynski | H04L 67/1021 |
| 2020/0296155 A1* | 9/2020 | McGrath | G06F 9/5027 |
| 2021/0014114 A1* | 1/2021 | Doshi | G06F 9/505 |
| 2021/0117249 A1* | 4/2021 | Doshi | H04L 67/1001 |
| 2022/0197773 A1* | 6/2022 | Butler | G06F 9/505 |

\* cited by examiner

*Primary Examiner* — Qing Yuan Wu
(74) *Attorney, Agent, or Firm* — Kilpatrick Townsend & Stockton LLP

(57) ABSTRACT

Techniques are disclosed for provisioning and managing a virtual edge device that is configured to emulate a physical edge device that executes within an isolated computing environment. The isolated computing environment may be separate from a centralized cloud computing environment that provides a plurality of services for executing customer workloads. In one example, a computer system receives a request to provision a virtual edge device. The computer system identifies a physical computing device to be provisioned as the virtual edge device based on the request. The computer system generates a set of data containers that containerizes a set of services configured to execute subsequent workloads, and then the system provisions the physical computing system with the set of data containers. In response to the customer request, the computer system provides a user interface operable for accessing and managing the virtual edge device.

20 Claims, 18 Drawing Sheets

Provision Virtual Edge Device ← 1201

Lab Details
② Add Compute Workload(s)
③ Add Storage Workload(s)
④ Review

Create Virtual Edge Device

This wizard will walk you through the process of creating a new Virtual Edge Device which you can use to test workload configurations and preview your Edge Device before your order hardware.

First, we need some details for the type of Edge Device you'd like to create.

Device Name

[ demo ]

Root User Password

[ •••• ]

Description *Optional*

[ demo ]

Cluster Size

CLOUD EDGE DEVICE VIRTUALIZATION

CROSS-REFERENCE TO RELATED APPLICATIONS

This non-provisional application claims priority to U.S. Patent Application No. 63/173,244, filed on Apr. 9, 2021, entitled "Cloud Computing Edge Computing Device (Rover)," the disclosure of which is herein incorporated by reference in its entirety for all purposes.

BACKGROUND

In cloud computing, processing and storage is generally performed by one or more service providers implemented at a centralized location. Data can be received from customers at the centralized location, processed there, and then the processed (or other) data can be transmitted back to customers. However, having a centralized location for cloud infrastructure components may not be ideal in various scenarios. For example, when there are hundreds or thousands of Internet of Things (IoT) devices transmitting data to the central servers, and especially when those IoT devices are not geographically close to the cloud infrastructure computing devices, conventional centralized systems are not ideal. These IoT devices may be considered on the "edge," as in they are not close to the central servers.

Additionally, there may be other instances when the centralized location for cloud components is less than ideal. For example, if the data is collected (e.g., by IoT devices) in a disconnected region or a location with no Internet connectivity (e.g., remote locations). Current centralized cloud computing environments may not meet time sensitivity requirements when streaming data due to the inherent latency of their wide-area network connections. Remotely generated data may need to be processed more quickly (e.g., to detect anomalies) than conventional centralized cloud computing systems allow. Thus, there are challenges with managing a traditional cloud computing environment that relies on centralized components. Another challenge is that it is often difficult for customers to efficiently determine if data processing jobs, which may be currently performed in a centralized cloud computing environment, are suitable for deployment on a device outside the centralized cloud.

BRIEF SUMMARY

Techniques are provided (e.g., a method, a system, non-transitory computer-readable medium storing code or instructions executable by one or more processors) for provisioning and managing a virtual edge device that is configured to emulate a physical edge device that executes within an isolated computing environment. The isolated computing environment may be separate from a centralized cloud computing environment that provides a plurality of services for executing customer workloads. In some embodiments, the virtual edge device may enable customers to efficiently test (e.g., prior to actual deployment on a physical edge device) how a customer workload, which may be executed in the centralized cloud computing environment and/or originally generated by the virtual edge device, would perform on an actual physical edge device. Various embodiments are described herein, including methods, systems, non-transitory computer-readable storage media storing programs, code, or instructions executable by one or more processors, and the like.

In one example, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method. The computer-implemented method may include implementing a centralized cloud computing environment of a cloud service provider, the centralized cloud computing environment providing a plurality of services for executing customer workloads. The method also may include receiving, by a computer system of the cloud service provider, a customer request to provision a virtual edge device to be operable for executing a customer workload. In some embodiments, the virtual edge device may be configured to emulate a physical edge device that selectively executes within an isolated computing environment having no access to a public network while executing within the isolated computing environment. The method also may include identifying, by the computer system from a plurality of physical computing devices, a physical computing device to be provisioned as the virtual edge device based at least in part on the customer request. The method also may include generating, by the computer system, a set of data containers that containerizes a set of services configured to execute subsequent customer workloads. The method also may include provisioning, by the computer system, the physical computing device with the set of data containers. The method also may include, in response to the customer request, providing, by the computer system, a user interface operable for accessing the virtual edge device. Other embodiments of this aspect may include corresponding computer systems, apparatus, and computer programs recorded on one or more computer storage devices, each configured to perform the actions of the methods.

Implementations may include one or more of the following features. For example, one feature may correspond to a computer-implemented method where the virtual edge device has a first hardware profile that differs from a second hardware profile of the physical edge device by less than a threshold amount. The threshold amount may indicate at least one of: (i) a similar degree of performance between executing a customer workload at the physical edge device and executing the customer workload at the virtual edge device or (ii) whether a customer workload that is executing in the centralized cloud computing environment is compatible with execution at an edge device. In some embodiments, the computer-implemented method may include:
receiving, via the user interface, a request to execute a workload of the subsequent customer workloads associated with the set of services; and executing, at the physical computing device that was provisioned as the virtual edge device, the workload utilizing at least one of the set of services in accordance with the request. In some embodiments, executing the workload at the provisioned virtual edge device emulates executing the workload at the physical edge device.

In some embodiments, the virtual edge device may be one of a plurality of virtual edge devices configured to operate as a distributed computing cluster, and the method further may include: receiving, via the user interface, a request to execute a workload; and executing, by the distributed computing cluster, one or more operations corresponding to the workload. In some embodiments, the physical computing device may be a bare metal device dedicated to a single customer. In some embodiments, the computer-implemented method may include: receiving, via the user interface, a request to generate a new workflow via the virtual edge device; generating the new workflow; and in response to a second request via the user interface, exporting the new workflow to the physical edge device that was emulated by the virtual edge device. Implementations of the described techniques may include hardware, a method or process, or computer software on a computer-accessible medium.

Some embodiments disclose a computing system of a cloud service provider comprising a memory comprising computer-executable instructions that, when executed with one or more processors of the computing system, cause the computing system to perform the method disclosed above.

Some embodiments disclose a non-transitory computer-readable storage medium comprising computer-executable instructions that, when executed with one or more processors of a computing system (e.g., a computing system of a cloud service provider), cause the computing system to perform the method disclosed above.

BRIEF DESCRIPTION OF THE DRAWINGS

FIG. 12 illustrates a user interface utilizable for provisioning a virtual edge device, according to some embodiments;

DETAILED DESCRIPTION

Figure 1:
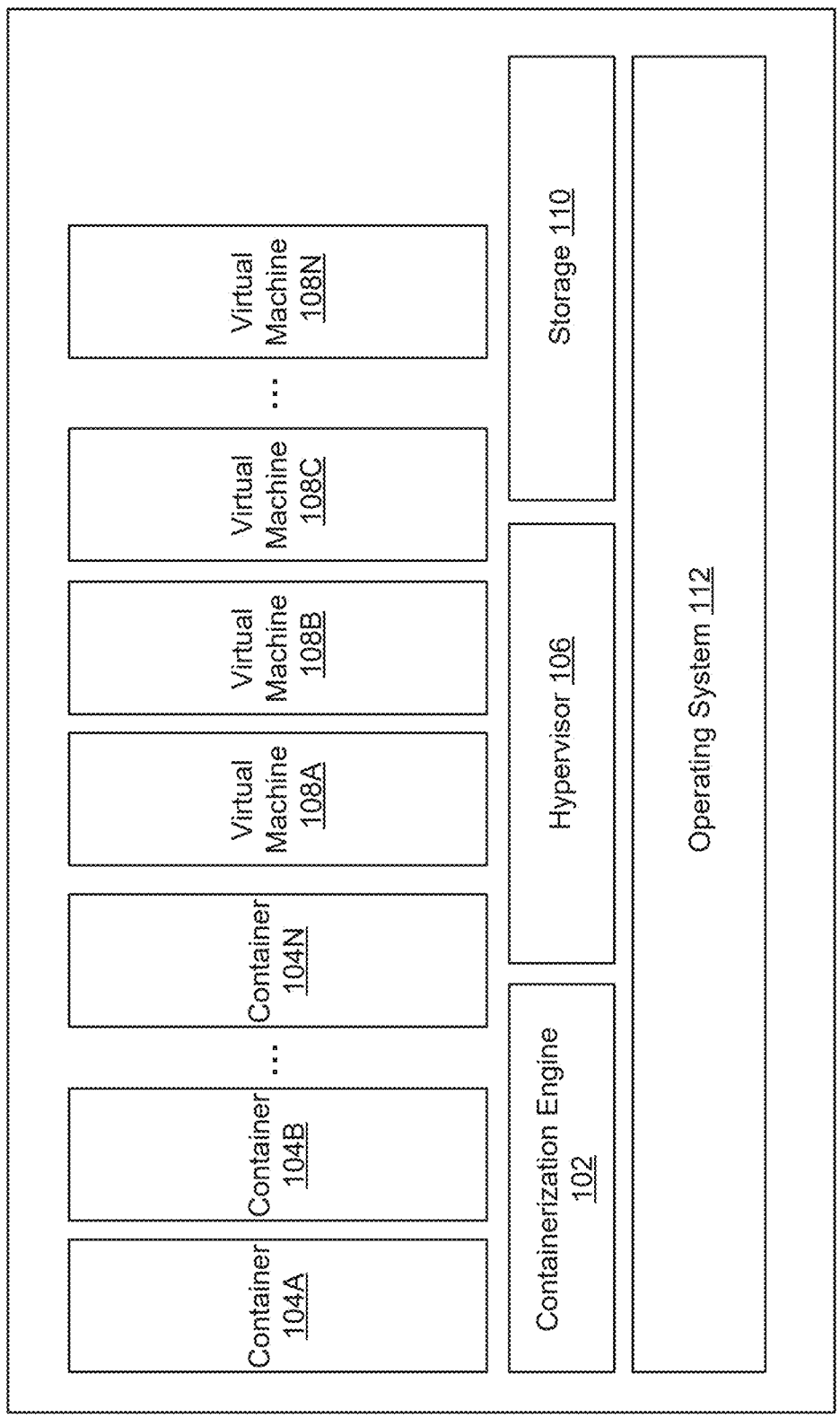
FIG. 1 is a block diagram of an example high-level architecture for a cloud infrastructure edge computing device, according to at least one embodiment.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

INTRODUCTION

In some examples, a cloud-integrated edge service (e.g., implemented in an edge computing device) may be integral in addressing the desire to run time-sensitive cloud infrastructure application outside of a centralized data center (e.g., a datacenter of a cloud infrastructure service provider). Such an edge computing device may deliver computing and storage at the edge and/or in disconnected locations (e.g., remote locations separate from the centralized data center and lacking a public/private network connection (e.g., an Internet connection, a VPN connection, a dedicated connection, etc.) to enable low-latency processing at or near the point of data generation and ingestion. In some instances, a fleet of portable (which may be ruggedized for protection) server nodes (e.g., a fleet of edge devices) may be configured to physically bring the cloud infrastructure service to remote locations where cloud technology has been considered technologically infeasible or too cost prohibitive to implement.

To a customer (e.g., a user), the edge computing device can act as an extension of their cloud infrastructure: including virtual machines (VMs), containers, functions and data files, block volumes or object store services can also be delivered from the cloud infrastructure tenancy (e.g., a tenancy of the centralized cloud computing environment) with little to no modifications, and the customer experience may remain unchanged from that of the centralized cloud computing experience. Additionally, the edge computing device may be configured to implement both a control plane and a data plane that are part of a cloud infrastructure service provider. The data plane can be configured to manage data storage, migration, processing, etc., while the control plan can be configured for controlling the various services and architecture components of the computing device. Once the edge computing device is properly connected to a customer computing device (e.g., via a local area network (LAN)), the customer may be able to utilize the IaaS service (or at least a subset of it) using the same SDK and API used with the centralized cloud service.

The edge computing device can be delivered to a customer in a pre-configured form, such that the only action that might be required of the customer is to connect the nodes to a network (e.g., a local/on premise network that is accessible by a user computing device), power them up, and/or log in. The device can be pre-configured in various ways based on customer preference/request, or it can be in one of various configurations (e.g., storage-centric, compute-centric, etc.). The node or cluster of nodes can be portable and is intended to be mobile—when moved and set up again (or used while in motion), the deployment continues to run from where it turned off (or continuously). The edge computing device can also monitor for wide area network (WAN) connection availability (e.g., the Internet or the like), and can synchronize customer and management data with the cloud once connected to a WAN.

Some potential use cases for the edge computing device include: storage and processing, compute and input/output (I/O) intensive applications, machine learning, remote computing, low latency database and analytics, and data collection and migration. More specifically, the edge device can be used for storage and processing of large volumes of images, video, audio, and IoT sensor data generated in environments where WAN connection is latent or unavailable (e.g., in remote areas, an oil off-shore platform, or the like). Once this data is pre-processed, filtered, compressed, and/or secured it may be transported or transferred to the cloud service provider, where it can be further processed by the centralized server (e.g., traditional cloud service provider). The device can also be used for compute and I/O intensive applications, where low latency is paramount, such as tactical reconnaissance or 5G communications. The device can also be used for machine learning, with models trained in the cloud and running in disconnected locations to improve efficiency, intelligence, and/or productivity in manufacturing, document management, transportation, oil and gas mining, and/or telecommunications. It can also be used for remote computing requiring elevated security and airtight containment of data. Additionally, the device can be used for low latency database and analytics workloads, with more applications optimized over time. Further, the device can also be used for data collection and migration of large sets of object and database management system (DBMS) data into a cloud service provider, e.g., at faster speeds and lower cost than a WAN transfer.

The edge device can natively support distributed cloud paradigms, where complex, multi-stage compute workflows can be separated into individual components, which in turn can be deployed to the infrastructure of the edge device, on premise, and/or in the cloud. An example of such distributed workflow is represented in the following scenario. Massive amounts of data can be collected by an edge computing node deployed on an airplane (e.g., a military jet) in a reconnaissance operation with no Internet access (e.g., a disconnected edge computing device), where this data is be pre-processed in near real time by a machine learning model previously trained by the cloud service provider that provided the edge device. Even the first pass of processing the data with the models can detect significant anomalies and can alert personnel immediately—for example, a bridge may be destroyed and therefore the troops should be rerouted. When the airplane lands, the edge computing device can be physically connected to a network (e.g., an edge station potentially deployed at the airstrip). The pre-processed, filtered, smaller dataset can be loaded for final processing to a cluster of edge computing device nodes at the edge station. The original edge computing device can be released and can be loaded on another (or the same) airplane, for example to support the next mission. When processing at the edge station is complete, a 3D map update can be issued for immediate use. Change sets can then be uploaded by the edge station cluster to a datacenter and can be used to build future models providing intelligent tactical forecasts to the reconnaissance operation, or the like.

It should be appreciated that the following techniques may be employed in a variety of contexts such as telecommunications, oil and gas, healthcare, hospitality, agriculture, transportation, and logistics, and the like.

Embodiments described herein address these and other problems, individually and collectively. Specifically, embodiments of the present disclosure provide for a cloud infrastructure edge computing device.

Edge Device Architecture

An edge computing device (sometimes referred to as "a cloud edge device" or an "edge device," for brevity), extends a user's centralized cloud computing tenancy by physically putting customer infrastructure and platform services where data is generated—on the edge, on premise, or completely disconnected. Each deployment is created to address specific customer needs by provisioning VM instance images and data from the customer's centralized cloud tenancy. These workloads remain fully functional offline as the edge device adapts to the connection state, operates in harsh environmental conditions, and is ready to sync with the cloud whenever the connection is re-established.

FIG. 1 is a block diagram of an example high-level architecture for a cloud infrastructure edge computing device (e.g., edge device 100), according to at least one embodiment. An overview of the software and hardware component of the edge device 100 is provided below.

In some examples, the edge device 100 may include containerization engine 102 (e.g., Docker, Kubernetes, etc.) configured to implement one or more containers (e.g., corresponding to service(s) 104A, 104B, 104C, to 104N, collectively referred to as "service(s) 104"). A containerization engine (e.g., the containerization engine 102) may be container-orchestration system for automating computer application deployment, scaling, and management. In some embodiments, the containerization engine may be configured to provide OS-level virtualization to deliver software in packages called containers. These containers can be isolated from one another and utilize respective software, libraries, and configuration files, and can communicate with each other through well-defined channels. In some embodiments, service(s) 104 may include any suitable number of services (e.g., one or more). These services may implement at least some portion of centralized cloud capabilities. Each service may be stand-alone or operate as a distributed cluster. The edge device 100 may further include a hypervisor 106 configured to implement one or more virtual machines (e.g., virtual machines 108A, 108B, 108C, to 108N, collectively referred to as "virtual machine(s) 108" or "VMs 108").

In some examples, the edge device 100 includes storage 110 (e.g., object and/or block storage for storing local data). The edge device 100 includes operating system (OS) 112. In some embodiments, the OS 112 may be optimized for executing on an edge device and/or specific to execution on an edge device. OS 112 may be configured to manage the hardware of edge device 100 and supports a data plane of the services running on the edge device 100. The OS 112 may be configured to support a specific deployment type (e.g., a single edge device deployment, or a specific edge device cluster configuration). The OS 112 may be configured to secure the edge device by disallowing direct access by customers.

In some embodiments, the edge device 100 may include hardware such as any suitable number of central processing units (CPUs) and/or storage drives. For example, the edge device 100 depicted in FIG. 1 may have one, two, or more CPUs, with various numbers of cores per processing unit, and it may include any number of storage drives (e.g., 6.4 terabyte (TB) drives, or the like). As a non-limiting example, the edge device 100 may include block and/or object storage of any suitable size. The edge device 100 may include any suitable number of central processing units (CPUs), graphics processing units (GPUs), random access memory (RAM) of any suitable size, one or more ports (e.g., QSFP28, RJ45, dual ports, etc.), tamper-evident seals, or any suitable combination of the above components.

In some examples, the basic system functionality/services can be accessed via RESTful APIs have a custom load of software based on Linux. The virtual machine(s) 108 may individually be a Kernel-based Virtual Machines (KVM) and/or a hardware-based Virtual Machine (QEMU). Although storage 110 is represented as a separate component from the container(s) 104 and VM(s) 108, it can run as a container (e.g., container 104A) or in a VM (e.g., VM 108A). In some examples, it may be favorable to implement the storage 110 (e.g., object storage, block storage, etc.) as a container.

Figure 2:
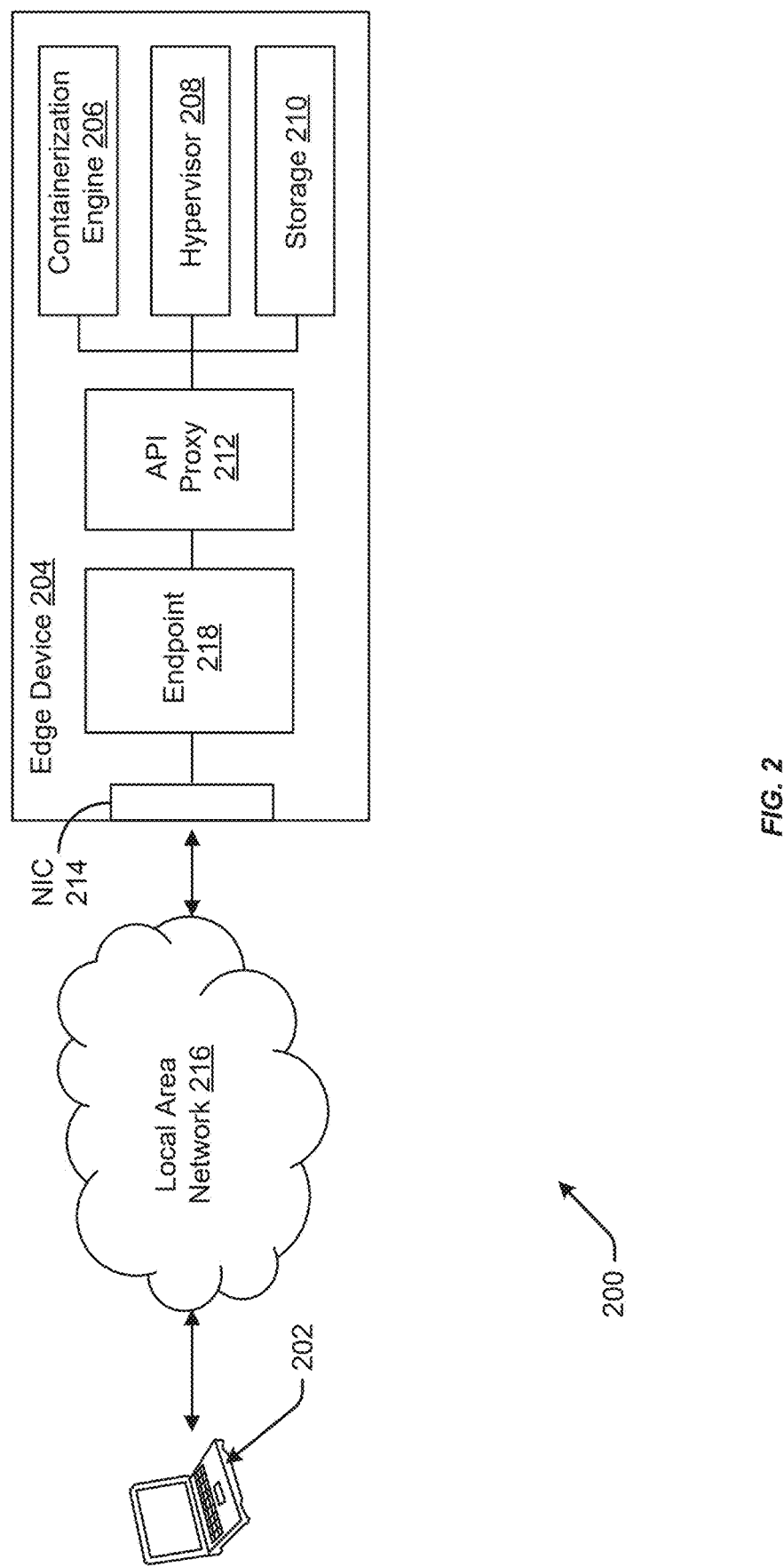
FIG. 2 is a block diagram of an example architecture for connecting a user computing device to a cloud infrastructure edge computing device, according to at least one embodiment.

FIG. 2 depicts an example architecture 200 for connecting the edge device described herein (e.g., edge device 100 from FIG. 1) to a computing device 202 (e.g., a user computing device). The computing device 202 can be any type of computing device including, but not limited to, a laptop computer, a desktop computer, or the like. The edge device 204 (an example of the edge device 100 of FIG. 1) may include containerization engine 206 (an example of the containerization engine 102 of FIG. 1), hypervisor 208 (an example of the hypervisor 106 of 1), and storage 210 (an example of the storage 110 of 1).

Additionally, as mentioned briefly above, the edge device 100 may include an API proxy 212 for managing the RESTful API calls received from the computing device 202. The API calls may enter the edge device 204 via network interface card (NIC) 214 that is internal to the edge device 204. The network interface card 214 may be used to connect the edge device 204 to the computing device 202 via a local area network (e.g., the LAN 216). The API calls received by the NIC 214 may be transmitted to an exposed endpoint that may implement a Web server (e.g., endpoint 218). The web server can transmit the requests to the API Proxy 212, which can route the requests to the appropriate service (e.g., containerization engine 206, hypervisor 208, and/or storage 210). The exposed endpoint/web server may also be configured to implement the lightweight console that is for use by the customer (e.g., the user interface displayed on the computing device 202).

The lightweight console can run within a web browser (e.g., Mozilla Firefox, or the like) on a laptop computer, desktop computer, or other network-accessible device (e.g., connected to the local area network (LAN 216)) that is network-connected to the edge device 204 (e.g., via a router, cable, etc.). The edge device 204 can expose the endpoint 218 for the console connection, and the web server can transmit data to the web browser of the computing device 202 over the LAN 216.

Figure 3:
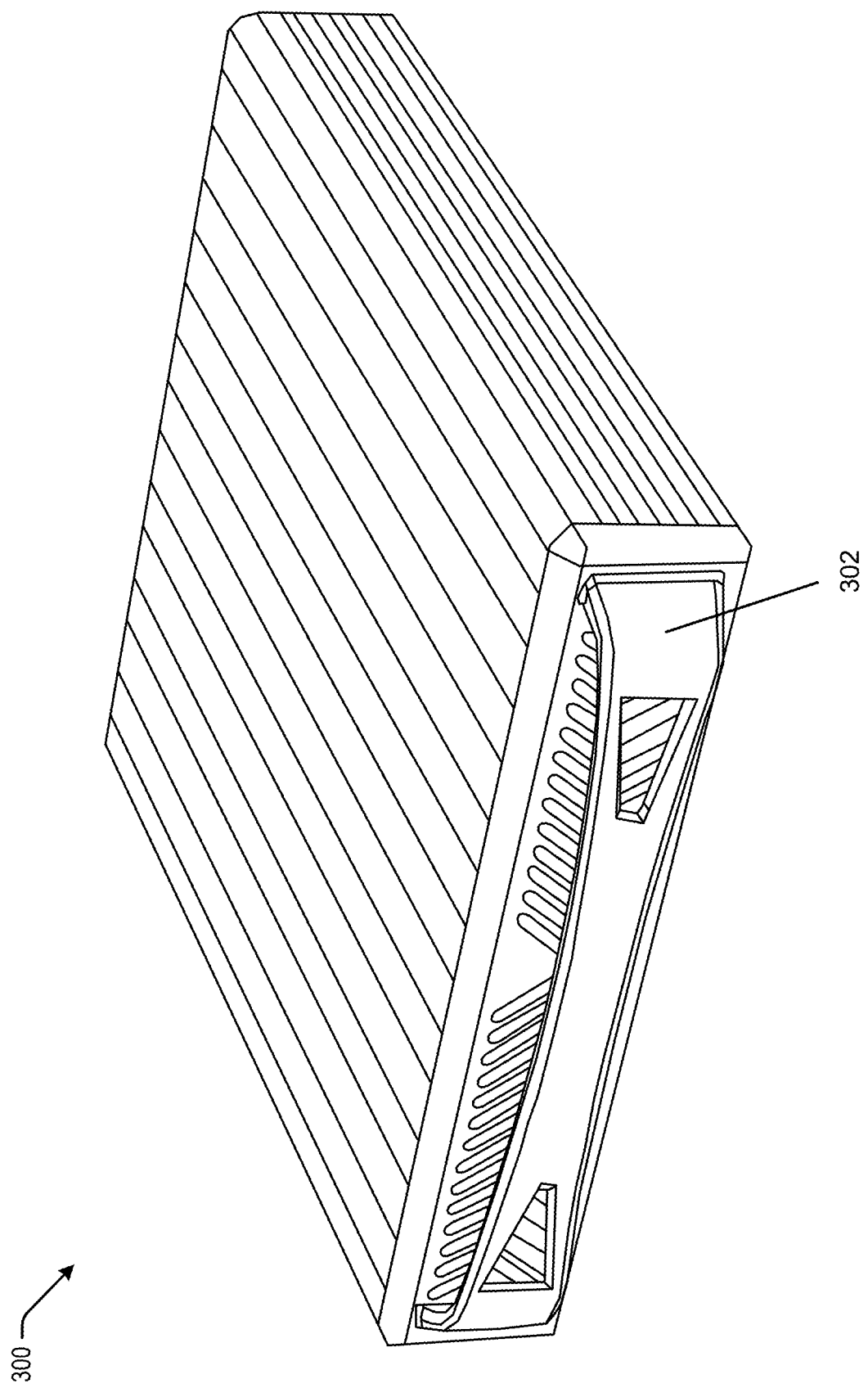
FIG. 3 is a block diagram of an example enclosure for a cloud infrastructure edge computing device, according to at least one embodiment.

FIG. 3 illustrates an example physical enclosure 300 of the edge device described herein (e.g., edge device 100 from FIG. 1). Various different form factors, shapes, colors, etc., can be employed to build a box (e.g., ruggedized) that can house the edge computing device. The physical enclosure can include handle 302, as shown, and may include tamper evident elements, so that if anyone breaks the enclosure open, it will be evident. In this way, the service provider that provides the edge computing device can ensure that the device is not modified. In some examples, the physical enclosure 300 may not be possible to open. However, in some cases, it might be possible, but it would require extreme measures.

Figure 4:
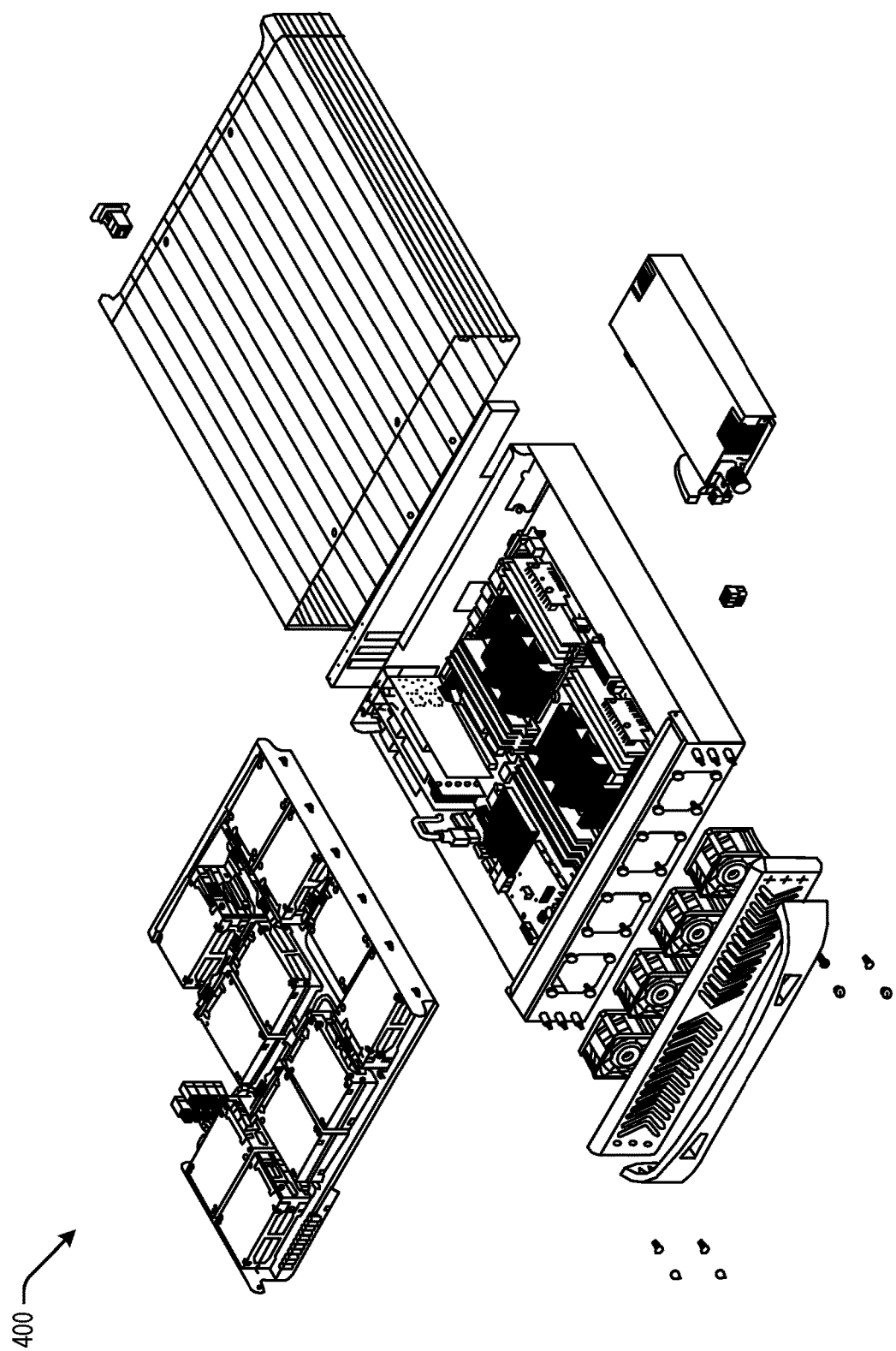
FIG. 4 illustrates an exploded view of the cloud infrastructure edge computing device described herein, in accordance with at least one embodiment.

FIG. 4 illustrates an exploded view of the cloud infrastructure edge computing device described herein (e.g., edge device 400, an example of the edge device 100 of FIG. 1), in accordance with at least one embodiment. The various components described with respect to FIGS. 1 and 2 can be communicatively attached to one or more motherboards and/or interface cards within the edge computing device 400. The illustrated configuration of components is but just one implementation. The specific locations of components shown is not intended to be limiting, and as noted, any configuration that is capable of implementing the functionality described herein is acceptable. Once the components are installed, the entire box can be closed, sealed, and locked with tamper-evident components.

The edge device 400 is a single enclosure. The enclosure may be designed to house any suitable number of serially attached SCSI (SAS) solid-state drives (SSDs) and all other components (e.g., CPU, memory, GPU, etc.) within the enclosure. The system may include one or more (e.g., 12 Gb) SAS connections to each drive in a fully contained sheet metal enclosure designed to fit within a standard 19" rack resting on an L bracket/shelf, on a table top or upright next to a desk with the use of a floor stand.

The system may include a tamper evident enclosure, front security plugs covering screws holding a front bezel in place with rear security interlock features. In some embodiments, the system may include a dual socket motherboard and any suitable amount of DRAM. In some embodiments, the system may include any suitable number (e.g., 2, 3, etc.) SATA SSDs, storage controllers, embedded network connections, one or more ports (e.g., dual ports, serial ports, etc.), one or more fans as part of a cooling system, or any suitable combination of the above.

As a non-limiting example, the edge device 400 may be made up of an external extruded aluminum case secured in the front with a vented bezel and rear panel only exposing I/O connections required for data transfer and management. Mounting can be designed to mount the any suitable motherboard, fans, and power supply.

Figure 5:
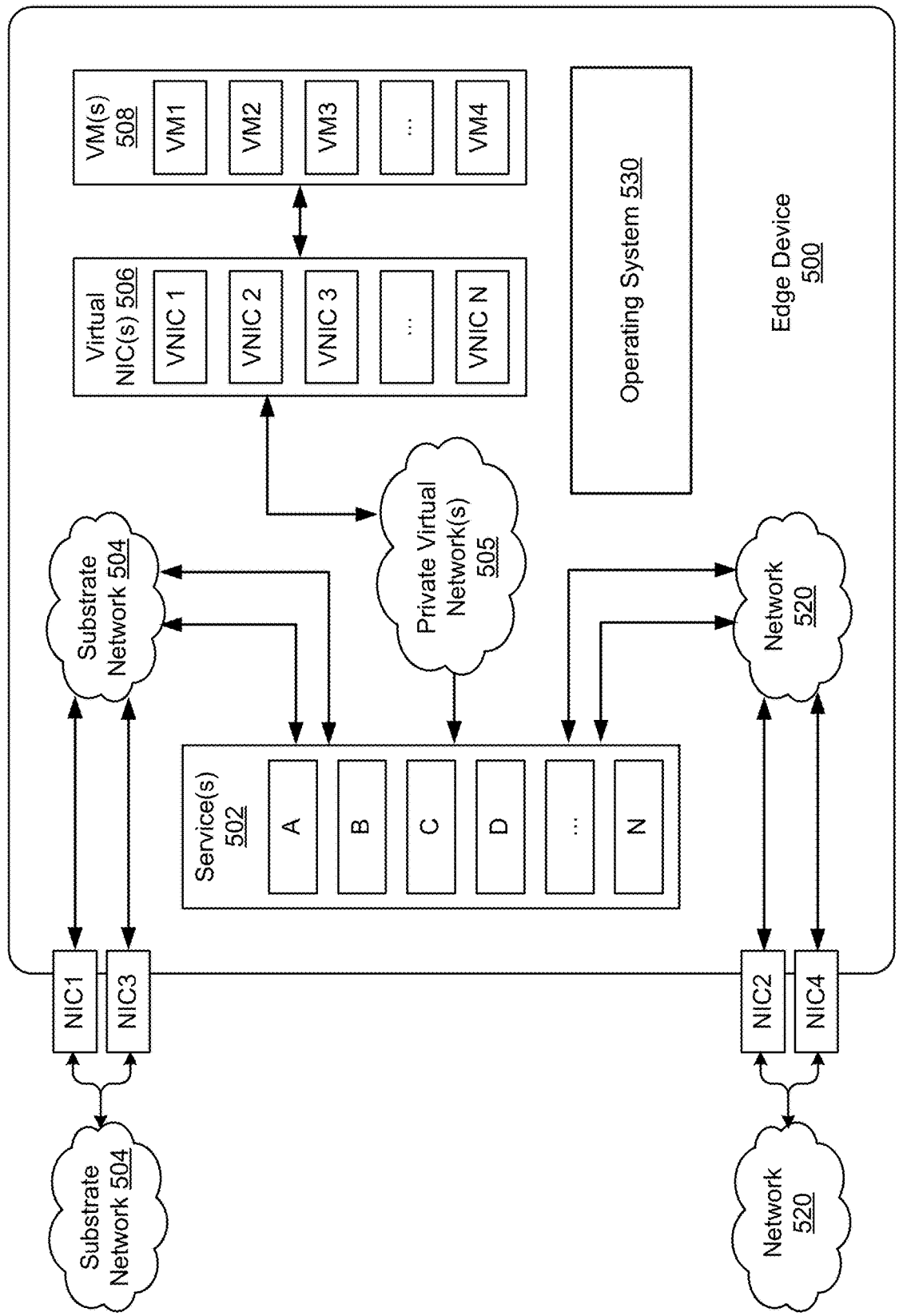
FIG. 5 is a block diagram of an example computer architecture of a cloud infrastructure edge computing device, according to at least one embodiment.

FIG. 5 is a block diagram of an example computer architecture 500 of a cloud infrastructure edge computing device (e.g., edge device 500, an example of the edge devices 100 and 204, of FIGS. 1 and 2, respectively), according to at least one embodiment. The edge device 500 can be thought of as a cloud-integrated service that extends some or all of conventional cloud capabilities to locations outside of cloud data centers. This can be achieved via portable ruggedized server nodes that provide cloud-like functionality in locations with no WAN connectivity. This allows customers to shift select cloud workloads to remote locations and enable intensive data processing operations close to the data ingestion points at the edge of their cloud infrastructure.

The edge device 500 may include any suitable number of services (e.g., service(s) 502). Each service may run as a container (e.g., a Docker container) locally on the edge device 500. The service(s) 502 may be communicatively connected via a substrate network 504 such that the communications between services are encrypted (e.g., in accordance with a security protocol such as MACsec). Each container may be assigned a substrate IP address (e.g., a static address) with which traffic can be addressed. In some embodiments, a security protocol (e.g., MACsec) is configured at provisioning time (e.g., before the edge device 500 is shipped to the user). The edge device's system software (including service(s) 502) may execute in the secure environments protected by boot security software (e.g., Trenchboot Secure Launch). Users may be restricted from accessing the secure environment and/or the substrate network 504. To minimize the amount of resources used by these services the service code may be compiled and saved to disk to decrease RAM space as well as decrease the CPU load on the edge device 500.

Some example services included in service(s) 502 may include a UI console service, an identity control plane (CP) service, an identity data plane (DP) service, a compute application programming interface (API) service, a compute worker thread service, a virtual network (VN) API service, a block storage API service, a function-as-a-service service, an events service, an object storage management service (e.g., implementing a storage platform such as Ceph Storage), a compute DP service (e.g., an example of hypervisor 208 of FIG. 2), a VN DP service, a block storage management service, a function-as-a-service API service, a function-as-a-service load balancing (LB) service, a function-as-a-service process thread service, a distributed data store management service (e.g., etcd3), a dynamic host configuration protocol service, a domain name system service, a network time protocol (NTP) service, to name a few. Some example functionality provided by these services is discussed below.

By way of example, compute DP service may be configured (e.g., preconfigured and provisioned onto the edge device 500) to isolate the VM(s) 508 on the same hypervisor host. The compute DP service can utilize any suitable container engine (e.g., Docker container, MicroContainer, or the like) to isolate the VM(s) 508 on the same hypervisor host from each other. The compute DP service may utilize any suitable hypervisor (e.g., Quick EMUlator (QEMU), Kernel-based Virtual Machine (KVM), etc.) to provide virtual hardware emulation for VM(s) 508. In some embodiments, VNIC(s) 506 are attached to subnets of any suitable number of virtual networks (e.g., private virtual network(s) (PVN(s))) 505 and are assigned private Internet Protocol (IP) addresses. One VM may have multiple VNICs from different VCNs and different subnets. The maximum number of VNICs can be limited by predefined thresholds (e.g., configuration data referred to as "VM shape" that defines VNICs per VM count, VNIC shape, etc.). In some embodiments, the predefined thresholds are applied to each of the VM(s) 508. The subnets utilized by the VNIC(s) 506 may be isolated by VLANs. In some embodiments, some or all of the VNIC(s) 506 may be assigned public and/or private IP addresses. A public IP address is an address in the network(s) 520, while a private IP address refers to an IP address of the PVN(s) 505.

In some embodiments, the edge device 500 implements various networking functionality via a number of services such as a network address translation (NAT) service, a dynamic host configuration protocol (DHCP) service, a domain name system (DNS) service, a network time protocol (NTP) service, a metadata service, and a public API service). The metadata service may provide initialization data and other metadata to all VM(s) 508. In some embodiments, DHCP service assigns private IP addresses to each of the VNIC(s) 506, each of the VM(s) 508 having one or more VNICS. DNS service may provide domain name resolution to VM(s) 508 on the edge device 500. NTP may provide time synchronization to VM(s) 508. In some embodiments, a public IP service executing as part of service(s) 502 may enable a VM to access a public API without assigning the VM a public IP and without configuring a service gateway.

In some embodiments, at least one of the VM(s) 508 may implement block (or object) storage. In some embodiments, the hypervisor associated with a virtual machine may include a library that enables the hypervisor to use a distributed data storage platform (e.g., Ceph). The library may utilize a protocol associated with that storage platform (e.g., RADOS Block Device (RBD) to facilitate storage of block-based data. The distributed data storage platform may be implemented over multiple virtual machines. In some embodiments, the distributed data storage platform supports making snapshots and copying block volumes. VM images and VM block volumes can be Ceph block devices. In some embodiments, the VM(s) implementing the distributed data storage platform will use system reserved resources (e.g., 8 CPU cores, some of the total number of CPUs available on the edge device 500). For example in order to provision a boot volume, a block device image may be copied to a boot volume of the block device. The distributed data storage platform may use block devices include multiple nodes for redundancy. If some node fails then the block device can continue to operate. In some embodiments, the distributed data storage platform (e.g., Ceph), automatically recovers the block device data in case of a few node failures. Block storage may be utilized to store images for any suitable deployable resource. By way of example, an image may be utilized for launching VMs. In some embodiments, the image may correspond to a particular VM shape (e.g., a compute heavy VM, a GPU optimized VM, a storage VM, and the like).

Compute API service may support the following operations: 1) VM launch and terminate, 2) VM stop, start, reboot, 3) List VMs and/or get information on a specific VM, 4) obtain VM console history API, 5) obtain a VM snapshot, 6) attach/detach block volumes, and the like. In some embodiments, Compute API service can be used to call other services (e.g., compute DP service, identity DP service for authentication and authorization, etc.).

Some of the functionality of other services will be discussed in connection with FIG. 7. In general, although each service may not be discussed in detail herein, the general functionality provided by the service(s) 502 may include the functionality of cloud services provided by a remote cloud service provider. In some embodiments, the edge device 500 may be associated with a predefined region and/or realm such that some of the service(s) 502 may operate as if they were operating in a cloud computing environment, despite the fact they are operating on one or more local device(s) (one or more edge devices) as a single instance or as part of a distributed service that may have no or intermittent public network access to a cloud computing environment associated with the customer.

In some embodiments, the edge device 300 may provide any suitable number of virtual networks (e.g., private virtual network(s) 505) using compute, memory, and networking resources (e.g., virtual network interface card(s) (VNIC(s)

506)). A virtual network is a logical network that runs on top of a physical substrate network. Using the service(s) 502, one or more customer resources or workloads, such as virtual machines (e.g., virtual machine(s) (VM(s)) 508, executing a compute instance) can be deployed on these private virtual networks. Any suitable combination of VM(s) 508 can execute functionality (e.g., a compute instance, storage, etc.) which is individually accessible through a virtual NIC (e.g., one of the virtual NIC(s) 506). Each VM that is part of a PVN is associated with a VNIC that enables the VM (e.g., a compute instance) to become a member of a subnet of the PVN. The VNIC associated with a VM facilitates the communication of packets or frames to and from the VM. A VNIC can be associated with a VM when the VM is created. PVN(s) 505 can take on many forms, including peer-to-peer networks, IP networks, and others. In some embodiments, substrate network traffic of the service(s) 502 may be encrypted and/or isolated (e.g., by virtue of different PVNs or subnets) from network traffic of one or more the VM(s) 508 executing on the edge device 500.

The edge device 500 thus provides infrastructure and a set of complementary services that enable customers to build and run a wide range of applications (e.g., compute instances), services, and/or storage in a highly available, physically local, and virtual hosted environment. The customer does not manage or control the underlying physical resources provided by the edge device 500 but has control over expanding or reducing virtual machines (e.g., compute instances, virtual NICs, block or object storage, etc.), deploying applications to those virtual machines, and the like. All workloads on the edge device 500 may be split into different CPU sets (e.g., VM and non-VM). One set (e.g., non-VM such as workloads performed by the service(s) 502) may utilize a subset of CPU cores (e.g., 8) of the edge device 504, while the other set (e.g., VM workloads performed by the VM(s) 508) may utilize a different subset of CPU cores.

The edge device 500 may be communicatively connected to a user device (e.g., the computing device 202 of FIG. 2) via one or more network interfaces (e.g., NIC2 and/or NIC 4) and network 520 to interact and/or manage the VM(s) 508. In certain embodiments, a lightweight console can be provided at the user device via a web-based user interface that can be used to access and manage the edge device 500. In some implementations, the console is a web-based application (e.g., one of the service(s) 502) provided by the edge device 500.

FIG. 5 depicts a single edge device. However, it should be appreciated that more than one edge device may be utilized as a distributed computing cluster.

Figure 6:
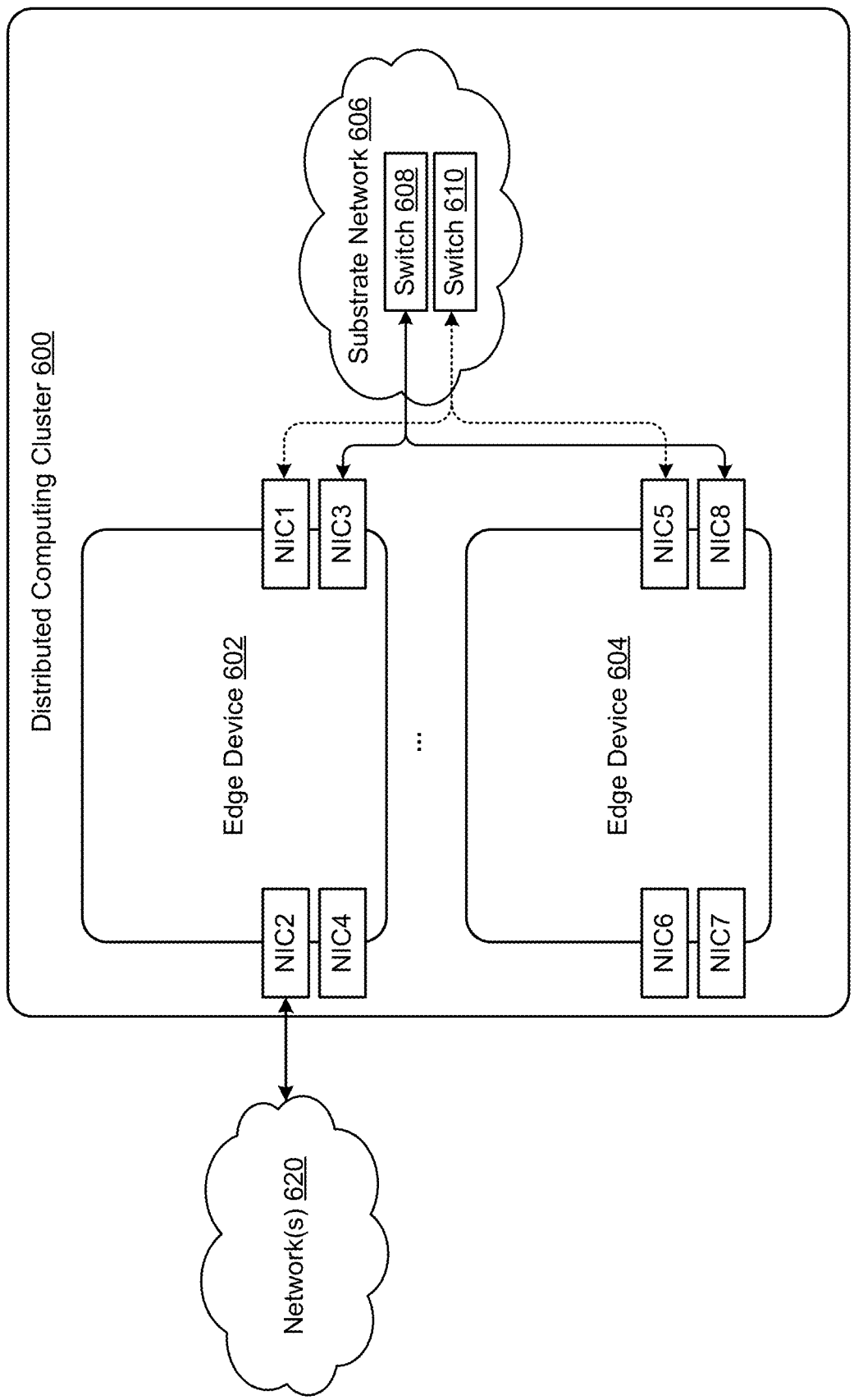
FIG. 6 is a block diagram depicting a distributed computing cluster that includes one or more edge computing devices, according to at least one embodiment.

FIG. 6 is a block diagram depicting a distributed computing cluster 400 that includes one or more edge computing devices (e.g., edge device 602 and 604, each an example of the edge device 500 of FIG. 5), according to at least one embodiment.

Each edge device of the distributed computing cluster 600 may be connected via substrate network 606 (an example of the substrate network 504 of FIG. 5. In some embodiments, the edge devices of the distributed computing cluster 600 (sometimes referred to as "edge computing nodes" or "edge nodes") may be connected by the substrate network 606 using one or more switches (e.g., switch 608 and/or 610). In some embodiments, NIC1 and NIC5 may include a particular connector (e.g., RJ45 connector) while NIC3 and NIC8 may include the same or a different connector (e.g., a QSFP28 100 GbE connector). In some embodiments, only one edge device of the distributed computing cluster 600 is connected to a customer network such as network(s) 620 (an example of the network(s) 520 of FIG. 5). Thus, not only may traffic between services of an edge device be encrypted and isolated from other traffic of a given edge device, but traffic between distributed services operating across multiple edge devices may also be encrypted and isolated from other traffic of the computing cluster. In some embodiments, each edge device is preconfigured as a particular node in the distributed computing cluster 400. In other embodiments, the user can configured the number and topology of the edge devices of the distributed computing cluster 600.

Figure 7:
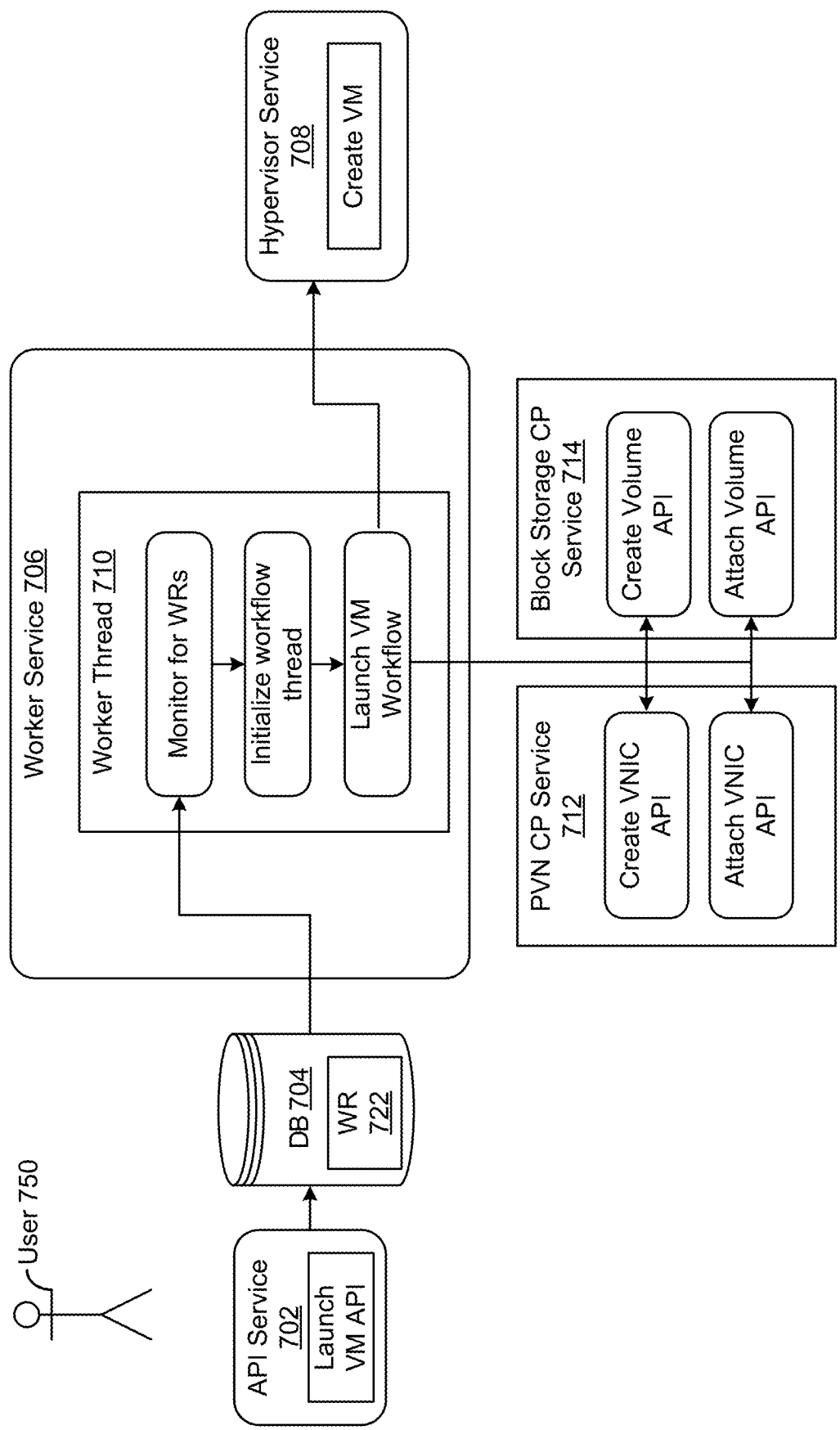
FIG. 7 is a block diagram depicting a control plane and flow for executing a workflow by one or more components of a cloud infrastructure edge computing device, according to at least one embodiment.

FIG. 7 is a block diagram depicting a flow 700 for executing a workflow by one or more components of a cloud infrastructure edge computing device, according to at least one embodiment. Components that execute the flow 700 may include API service 702, database 704, service 706, hypervisor service 708, PVN CP service, Block storage CP service 714, although more or fewer services may be included. In some embodiments, each of the services of FIG. 7 are an example of a service of the service(s) 502 of FIG. 5, of which. In some embodiments, at least some of the functionality discussed in connection with the services of FIG. 7 may be combined in any suitable combination and provided as a single service or instances of the same service. By way of example, in some embodiments, the functionality of services 702-708 may be provided by a single service (e.g., compute CP service discussed above in connection with FIG. 5). In some embodiments, the functionality provided by the services 702-708 may be provided by a single edge device (e.g., edge device 500 of FIG. 5) or by two or more edge devices (e.g., by edge device 602 and edge device 604 of FIG. 6).

In some embodiments, the API service 702 may be configured to accept work requests that include intended state data that describes an intended state of a set of data plane resources (e.g., VM(s) 508 of FIG. 5). As a non-limiting example, user 720 may utilize a user device (e.g., the user device 202 of FIG. 2) to access a user interface with which he can make various selections indicating a desire to launch a VM. The user input may be received by the API service 702 (an example of the compute CP service of FIG. 5) which may generate a work request (e.g., WR 722) and utilize a predefined Launch VM API to store the work request in a distributed database (e.g., DB 704). In some embodiments, the DB 704 may be a computing cluster which is configured to use etcd3 as an immediately consistent, highly-available, transactional, distributed database. Generally, a work request indicates a desire and information needed to create and/or modify data plane resources such as VM(s) 508. In some embodiments, the work request includes state information indicating a desired state for the data plane resource. In some embodiments, the DB 704 may be accessible to all services operating on any edge device (and by services operating on any suitable edge device of an edge device cluster such as distributed computing cluster 600).

Service 706 (e.g., also an example of the compute CP service of FIG. 5) may be configured to execute one or more worker processes (e.g., computing thread 710). Some of these worker processes may be configured by the service 706 at any suitable time to execute a continuous and/or ongoing predefined workflow. By way of example, the service 706 may configure one or more worker threads (e.g., including computing thread 710) to monitor the DB 704 for new work requests (e.g., WR 722). The computing thread 710 may be configured to determine if a work request WR 722 is already being attended to. In some embodiments, this entails checking a predefined storage bucket within DB 704 for a unique identifier associated with WR 722. If the unique ID included within WR 722 does not appear in the bucket (or the WR is otherwise indicated as having not been picked up for processing), the computing thread 710 (e.g., a nanny thread) may initialize a workflow thread (e.g., another instance of a computing thread 710) which may then be configured by the computing thread 710 to execute a workflow corresponding to launching a VM corresponding to the WR 722.

The initialized workflow thread may be communicatively coupled (e.g., via the substrate network 502 of FIG. 5) to a workflow service (not depicted). The workflow service may be configured to identify, from one or more predefined workflows, one that corresponds to launching a VM, and therefore, to the work request 722. These predefined workflows identify one or more steps/operations to be taken, and a sequence to those steps, in order to achieve a predefined goal (e.g., launching a virtual machine, stopping/starting a virtual machine, terminating a virtual machine, creating a block volume, removing a block volume, etc.). The workflow thread may launch the VM workflow and oversee its execution by various other entities. In some embodiments, the workflow thread may pass any suitable portion of the intended state data of the DP resource to any suitable combination of services.

As a non-limiting example, as part of the workflow for launching a virtual machine (e.g., a VM to be hosted by hypervisor service 708), one or more APIs can be called for creating and attaching the VNIC. Similarly, a number of APIs may be provided for creating and/or attaching a block storage volume API. In some embodiments, the workflow thread may perform any suitable call to one or more APIs to invoke the functionality of PVN CP Service 712, which in turn may be configured to create and attach a VNIC. The workflow thread may then call block storage CP service 714 which may then execute any suitable operations to create and attach a block storage volume. The worker thread overseeing the workflow may ensure a designated order (e.g., create the VNIC first before creating the block volume). This worker thread may be configured to catch any errors and/or exceptions from one or more services it has invoked. If no exceptions/errors are encountered, the worker thread overseeing the workflow can provide any suitable data to the hypervisor service 708 (via the substrate network), which in turn, execute functionality for creating the VM requested. The hypervisor service 708 may provide actual state data for the newly launched VM. In some embodiments, the worker thread overseeing the workflow can store the actual state data in the DB 704 for later reference (e.g., when a monitor may determine whether the actual state data matches the requested state data indicating no changes needed or when the actual state data fails to match the requested state data, indicating a change of the data plane resources is needed).

In some embodiments, the workflow thread may be communicatively coupled to a cluster manager (not depicted). Cluster manager may be configured to manage any suitable number of computing clusters. In some embodiments, the cluster manager may be configured to manage any suitable type of computing cluster (e.g., a Kubernetes cluster, a set of computing nodes used to execute containerized applications, etc.). The workflow thread may be configured to execute any suitable operations to cause the cluster manager to execute any suitable orchestration operation on the DP resource(s) (e.g., a VM) in accordance with the instructions identified to bring the DP resource(s) in line with the intended state data.

In some embodiments, a monitoring entity (e.g., the workflow thread, a thread launched by the workflow thread) may be communicatively coupled to DP resource(s) 116 and configured to monitor the health of DP resource(s). In some embodiments, the monitoring entity may be configured to store any suitable health data in the DB 704.

The specific operations and services discussed in connection with FIG. 7 is illustrative in nature and is not intended to limit the scope of this disclosure. The particular operations performed and services utilized may vary depending on the particular workflow associated with the requested operations.

In some embodiments of the present disclosure, techniques are disclosed for provisioning and managing a virtual edge device that is configured to emulate a physical edge device that executes within an isolated computing environment. In some embodiments, the physical edge device may be similar to edge device 100 of FIG. 1 and/or other edge devices described herein. As described herein, the isolated computing environment may be separate from a centralized cloud computing environment that provides a plurality of services for executing customer workloads. In some embodiments, the virtual edge device may correspond to a bare metal device that has similar characteristics (e.g., a similar hardware profile, such as an equivalent number of CPU cores and/or memory) as the physical edge device. In some embodiments, the virtual edge device may be associated with (e.g., located within) the centralized cloud computing environment, and may enable customers to test how a customer workload, which may be executed in the centralized cloud computing environment and/or originally generated by the virtual edge device, would perform on an actual physical edge device (e.g., prior to actual deployment of the customer workload on a physical edge device in the isolated computing environment).

To further illustrate, consider a scenario in which a cloud services provider (CSP) provides a service to one or more customers, for example, including an organization (e.g., a wildlife preservation organization) that operates in one or more remote areas of the world. In this example, the wildlife preservation organization may have several agents (e.g., personnel) located in a particular remote area, each agent being equipped to operate one or more measurement equipment (e.g., a camera, video recorder, an inertial measurement unit (IMU) tracker, etc.). For example, a particular agent's video recorder may regularly capture video of different types of wildlife in the remote area. Meanwhile, the organization may execute one or more services via a centralized cloud computing environment, whereby a service may be configured to execute one or more workloads. For example, a first service may correspond to a web server that hosts a website. The web server may be tasked with executing a workload that receives and processes web traffic from one or more agents that upload data (e.g., images, videos, tracking data) to the web server on a regular basis. A second service may be associated with analyzing the uploaded data. For example, the web server of the first service may relay (e.g., over a VPN) uploaded data to the second service, whereby a machine learning algorithm (and/or other heuristic model) may execute one or more workloads to analyze the uploaded data. For example, one workload may be associated with classifying types of wildlife shown in the images. Another workload may be associated with analyzing the environment (e.g., via video analysis, location analysis, etc.) in which the wildlife is located. It should be understood that any suitable workloads may be executed by the one or more services.

In this example, due in part to the large amount of data being regularly uploaded and analyzed (e.g., by multiple agents and/or devices of the organization), and, considering network latency (and/or other processing) constraints, the wildlife preservation organization may determine to utilize a physical edge device (e.g., edge device 100) to perform (e.g., offload) one or more of the workloads currently performed in the centralized cloud computing environment. The physical edge device may be intended to be located near the remote area, whereby latency bottlenecks may be reduced. However, before placing a request (e.g., a customer order) to provision the physical edge device and ship the device to the remote area, the organization may request to use (e.g., provision) a virtual edge device to efficiently verify that the physical edge device may be sufficient to meet their computing needs at the remote area. As described herein, a virtual edge device may correspond to a physical (e.g., bare metal) device that emulates the performance and/or reliability of the physical edge device. The virtual edge device may be associated with (e.g., located within) the centralized cloud computing environment, for example, located within an isolated lab of a data center that houses the centralized cloud computing environment. In this example, the isolated lab may include virtual edge devices that are partitioned (e.g., via a separate VPN) from other devices of the centralized cloud computing environment. In some embodiments, the virtual edge device may be selectively connected to the centralized cloud computing environment, for example, to synchronize data (e.g., upload and/or download workloads) between the virtual edge device and the centralized cloud computing environment.

Continuing with the example above, the organization may request to provision a physical computing device in the isolated lab as a virtual edge device. For example, a computer system of the CSP (e.g., located within and/or communicatively connected to the centralized cloud computing environment) may receive the request to provision the virtual edge device. The computer system may identify a particular physical computing device to be provisioned as the virtual edge device based on the request. For example, the computer system may identify the particular physical computing device as having a similar hardware profile as a physical edge device, such that the physical computing device may sufficiently emulate the physical edge device. The computer system then may generate a set of data containers that containerizes a set of services configured to execute subsequent workloads. For example, data containers may containerize services corresponding to the web server and/or associated VPN resources, the one or more machine learning models that execute workloads, one or more storage units storing data (e.g., images, videos), etc. Note that, as described above, although the physical computing device may be isolated from other components of the centralized cloud computing environment (e.g., in an isolated lab, thus providing a similar environmental context as may be expected for a physical edge device), a low-latency VPN may be selectively configured and/or maintained between the physical computing device and the centralized cloud computing environment, thus enabling efficient data synchronization of workloads. The computer system may efficiently download containers for existing workloads from the centralized cloud computing environment to the physical computing device over the VPN (and/or vice versa, relating to uploading data). In this manner, the virtual edge device may be provisioned with workloads from the centralized cloud computing environment (e.g., to test how existing workloads may perform on a physical edge device), while also emulating a physical edge device's performance and/or reliability in the real-world (e.g., a remote region). Continuing with the illustration, the computer system may then provision the physical computing device with the set of data containers corresponding to the services provided by the virtual edge device that was requested by the customer. In response to the customer request, the computer system may further provide a user interface operable for accessing and managing the virtual edge device.

In this example, an administrator of the wildlife organization may log-in to the computer system, whereby the user interface may present information related to the provisioning and/or management of the virtual edge device. For example, the user interface may receive input to execute workloads that were provisioned to the virtual edge device via the containers. Upon the virtual edge device executing the workloads, the user interface may report one or more metrics. For example, the user interface may present information associated with the performance (e.g., memory consumption, CPU resources consumption, disk utilization, etc.) of the workloads on the virtual edge device. In some embodiments, the user interface may present information (e.g., one or more health indicators) indicating whether workloads were successfully executed on the virtual edge device and/or whether any issues were encountered. For example, a health indicator may indicate that one of the workloads did not successfully complete because the workload depended on a service that was not executing (e.g., and/or not executing properly) on the virtual edge device. In some embodiments, a health indicator (e.g., a green, yellow, or red visual indicator) may indicate whether a customer workload that is executing in the centralized cloud computing environment (e.g., and subsequently provisioned to an edge device) is compatible with execution at the edge device (e.g., and/or vice versa). Because a virtual edge device may emulate the physical edge device, the workload health indicator may also be indicative of whether execution of the workload on the physical edge device will be successful (e.g., compatible with the cloud computing environment) or not. It should be understood that the user interface provided by the computer system may be used for any suitable operations to manage the virtual edge device, including, but not limited to: provisioning a new virtual edge device, provisioning the virtual edge device with one or more customer workloads by downloading the workloads from the centralized cloud computing environment, decommissioning a virtual edge device, reviewing statistics associated with workload execution on the virtual edge device, configuring workload settings, generating (e.g., developing) new workloads on the virtual edge device, uploading workloads to the cloud, provisioning a physical edge device with a similar (e.g., same) configuration as an already-tested virtual edge device, etc. In this way, techniques herein may enable a user (e.g., the administrator of the wildlife organization) to test workloads on a virtual edge device prior to actual deployment on a physical edge device in the remote region. In some embodiments, the user interface may enable a customer to inspect operations of the virtual edge device to verify that the virtual edge device is adequate to execute the desired workloads. In some embodiments, the verification may be performed automatically be the system. For example, based in part on one or more metric indicators (e.g., compatibility indicators, performance indicators, etc.), the system may automatically verify that the virtual edge device is adequate to execute the desired workloads.

In some embodiments, once a customer has obtained verification that the virtual edge device is adequate to execute the desired workloads, the user may request to provision and ship a physical edge device to the customer (e.g., at a remote location). For example, using the illustration above, the user interface of the computer system may receive input to order a new physical edge device. The order may request that the existing configuration of the virtual edge device (e.g., the deployment of containers, workload settings, etc.) may be substantively replicated (e.g., snapshotted via an imaging process) on the physical edge device, such that, when the customer powers on the physical edge device at the remote location, the physical edge device is already configured to operate with the same settings that the virtual edge device (e.g., in the lab of the data center) was configured with. In this way, techniques herein enable a seamless end-to-end process for testing and provisioning workloads for execution on a physical edge device (e.g., in an isolated environment).

In some embodiments, a virtual edge device may be one of a plurality of virtual edge devices that are configured (e.g., and/or provisioned) to operate as a distributed computing cluster. For example, the virtual edge devices may respectively correspond to physical computing devices that are isolated in a lab of a cloud computing data center (e.g., similar to as described above). In some embodiments, the user interface may enable a customer to determine how many virtual edge devices will be provisioned, which workloads may be executed on (and/or across) different devices, a VPN associated with the distributed computing cluster, and other suitable settings. In this manner, techniques herein may also enable increased efficiency when scaling up to test for potentially deploying a cluster of physical edge devices (e.g., in a remote region). For example, the customer may want to provision one or more workflows (e.g., each workflow including a sequence of workloads) to the distributed computing cluster.

Embodiments of the present disclosure provide several technical advantages over conventional systems. For example, as described herein, it is often resource intensive for customers to determine if workloads that currently operate in the cloud are also compatible for successfully executing on an edge device (e.g., in a remote region). This process may require significant computing and/or human resources to test, and often may be subject to several rounds of iteration to eliminate any performance and/or compatibility issues. These inefficiencies may be even more compounded when considering that a customer may want to scale deployment of edge devices to a cluster of devices, executing more complex workflows in coordination with other devices and/or processes. Techniques herein enable improved efficiency and overall customer experience via a provisioning of one or more virtual edge devices. As described herein, by emulating a physical edge device via a virtual edge device, techniques enable a mechanism for reliably testing deployment of workloads (e.g., prior to actual physical deployment in the real-world). In some cases, this may be helpful when a customer already has existing workloads executing in the cloud, and they want a convenient mechanism to test (e.g., emulate) the performance of the same workloads on an edge device, while incurring minimal overhead costs (e.g., machine procurement, set-up time, tear-down time) to perform the testing. In some cases, a customer may also generate new workloads on the virtual edge device, which may be subsequently provisioned to a physical edge device and/or synchronized with the cloud. Thus, techniques provides a more seamless end-to-end testing and deployment process (e.g., between a centralized cloud computing environment, a virtual edge device, and/or a physical edge device).

Figure 8:
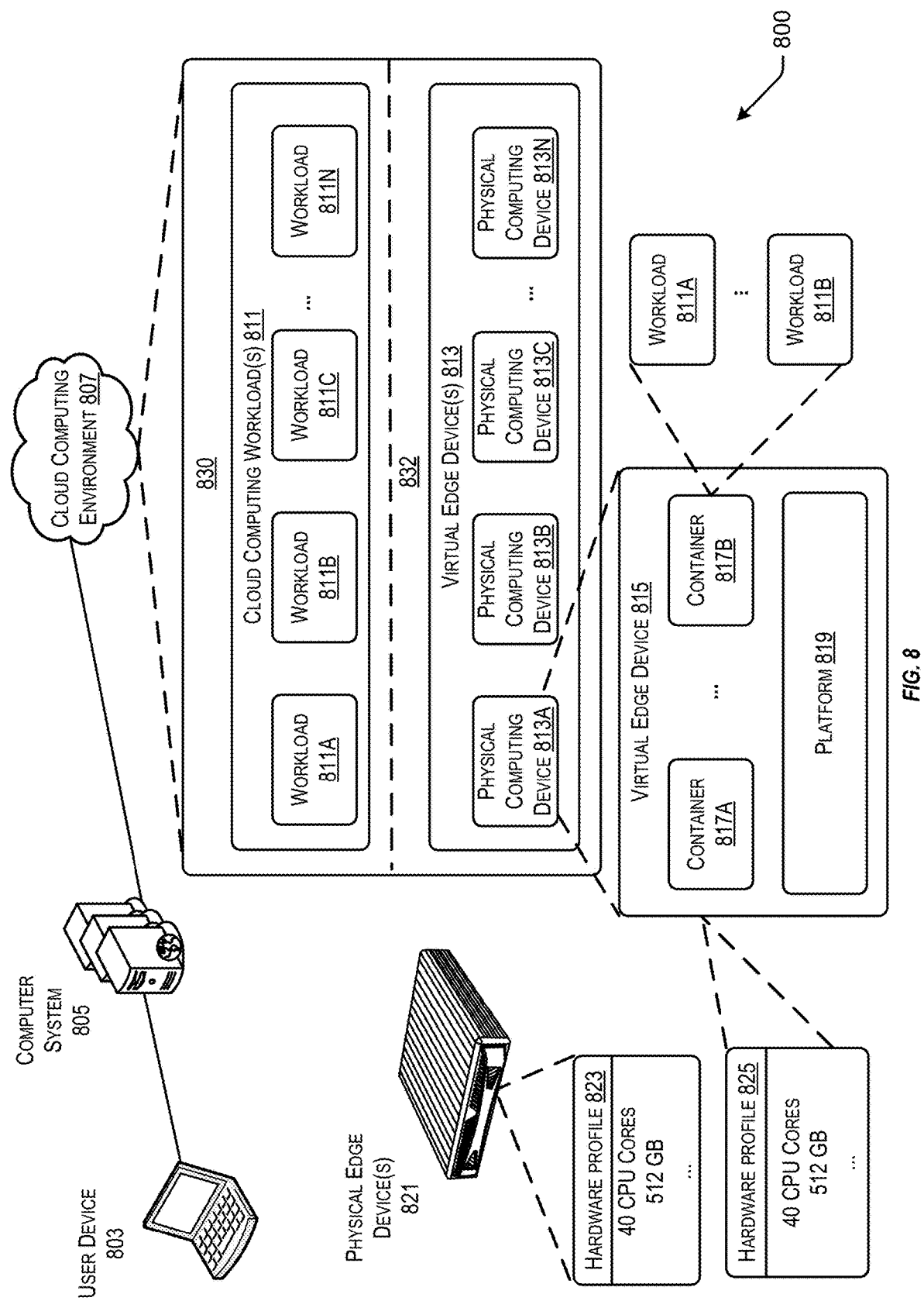
FIG. 8 is a simplified block diagram illustrating an example environment for provisioning a virtual edge device, according to some embodiments.

FIG. 8 is a simplified block diagram illustrating an example environment 800 for provisioning a virtual edge device, according to some embodiments. In FIG. 8, several elements are depicted, including user device 803, computer system 805, cloud computing environment 807, and physical edge device(s) 821 (e.g., which may correspond to any of the edge devices described in reference to FIGS. 1-7). In the illustration of FIG. 8, computer system 805 may be associated with a cloud services provider. The cloud services provider may further be associated with the cloud computing environment 807, which may include a plurality of devices, as described further herein.

In some embodiments, the computer system 805 may be tasked with, among other things, coordinating the provisioning and/or management of one or more virtual edge device(s) 813. For example, the computer system 805 may enable the provisioning of a physical computing device (e.g., physical computing device 813A) as a virtual edge device (e.g., virtual edge device 815). This provisioning may be performed based in part on synchronizing (e.g., containerizing and/or downloading over a VPN) a workload from a public portion 830 of the cloud computing environment 807 (e.g., one or more devices executing in a public portion 830 of the cloud computing environment 807) to a physical computing device (e.g., physical computing device 813A), which may be isolated within the cloud computing environment 807 (e.g., in an isolated portion 832 of the cloud computing environment, and/or network-partitioned).

In some embodiments, the computer system 805 may enable provisioning of a physical edge device. For example, the computer system 805 may provision physical edge device 821 with a similar (e.g., substantively the same) configuration that was previously provisioned to a virtual edge device, whereby the configuration (e.g., an operating system, core services, and/or one or more containers) is suitable to execute one or more workloads in an isolated environment (e.g., in a remote region of the world). As described further herein, it should be understood that the computer system 805 may facilitate data transmission (e.g., synchronization of data, including uploading and/or downloading data) between any suitable combination devices, for example, between one or more of physical edge device(s) 821, virtual edge device(s) 813 (e.g., devices 813A-N), and/or other devices of the cloud computing environment 807 (e.g., which may execute cloud computing workload(s) 811). In some embodiments, the computer system 805 may coordinate one or more cloud computing operations of the cloud computing environment 807.

Turning to the elements of FIG. 8 in further detail, user device 803 may be any suitable computing device that may communicate with other devices (e.g., via a network). For example, the computer system 805 may provide a user interface for presentation via a display connected to the user device 803. In some embodiments, the user device 803 may execute one or more operations via the user interface, for example, generating and/or managing cloud computing workload(s) 811, provisioning one or more virtual edge devices 813, provisioning one or more physical edge devices 821, etc. In some embodiments, the user device 803 may be a customer device (e.g., a laptop, PC, etc.) of a customer that has an account with the cloud services provider. In some embodiments, the user device 803 may be located outside (or within) the cloud computing environment 807 (e.g., at a customer premises) and/or connected via one or more networks (e.g., via the Internet, over a VPN, via WiFi, etc.). In some embodiments, the user device 803 may execute one or more applications (e.g., a web browser and/or other user applications). These applications may be used to present the user interface that is operable for interfacing with devices associated with the cloud services provider.

In some embodiments, computer system 805 may also be any type of computing device such as, but not limited to, a collection of virtual or "cloud" computing resources (e.g., associated with and/or located within the cloud computing environment 807), a remote server, a laptop computer, a desktop computer, a server computer, or a virtual machine instance. In some embodiments, the computer system 805 may be in communication with the user device 803 via one or more networks, as described herein. In some embodiments, the computer system 805 may be tasked with providing one or more user interfaces to the user device 803. The computer system 805 may receive input via a user interface and coordinate (e.g., orchestrate) one or more operations according to the input. For example, the computer system 805 may transmit instructions to provision a new virtual edge device or to provision a new physical edge device for shipment to the customer. It should be understood that the computer system 805 may be enabled to perform any suitable operations associated with management and/or provisioning of virtual edge devices 815 and/or physical edge devices 821.

In some embodiments, the cloud computing environment 807 may be associated with a centralized cloud computing environment, as described herein. For example, the cloud computing environment 807 may include a plurality of devices. The plurality of devices may be located at one or more data centers (e.g., in different geographic regions). The devices may correspond to servers, server clusters, racks, and the like. In some embodiments, the devices may be networked together and accessible via one or more networks (e.g., the Internet, a VPN, etc.). In some embodiments, the plurality of devices may be partitioned. For example, as introduced above, the portion 830 may include a set of devices that may be collectively used to execute cloud computing workloads 811 for customers within the centralized cloud computing environment. Using an earlier example for further illustration, a customer (e.g., a wildlife organization) may execute workloads 811A-811N in the centralized cloud computing environment. In this example, workload 811A may correspond to one or more services associated with maintaining a web server, for example, to receive uploads (e.g., images, videos, object tracking data, etc.) from agent devices in the field via a web portal maintained by the organization. Meanwhile, workload 811B may include a service that executes a machine learning algorithm to analyze images and videos received via the web portal. Workload 811C may include a storage service that collects and stores data process from workload 811B. It should be understood that one or more workloads may be organized into a workflow, as described herein. For example, workload 811A may execute one or more operations and then call another service to execute a portion of workload 811B. It should further be understood that any suitable number of workloads and/or workflows may be executed by a customer within the centralized cloud computing environment of portion 830.

Continuing with illustrating the cloud computing environment 807, portion 832 may correspond to another portion of the cloud computing environment 807 that is isolated from portion 830. For example, portion 832 may correspond to a lab environment (e.g., or other suitable computing environment) that is partitioned from other devices of portion 830. In this example, the lab environment of portion 832 may include one or more physical computing device (e.g., the plurality of physical computing devices 813A-813N). In some embodiments, physical computing devices of portion 832 may be dedicated to enabling a customer to test (e.g., approximate) how one or more workloads performs on a physical edge device (e.g., physical edge device 821), prior to the actual provisioning and deployment (e.g., shipment) of a physical edge device 821 to the customer. It should be understood that portion 830 and portion 832 may be partitioned via any suitable one or more mechanisms (e.g., in different geographic regions, in different locations within a particular data center, in different networks (e.g., different VPNs), etc.). For example, the portion 830 may be accessible via the public Internet, while the portion 832 (and/or clusters of devices within portion 832) may be isolated from the public Internet and/or accessible via a VPN.

In some embodiments, a particular physical computing device may be selected, from among physical computing devices, to be provisioned as a virtual edge device based on its ability to emulate a physical edge device. For example, using physical computing device 813A as a representative device, the physical computing device 813A may be initially a bare metal device (e.g., a device without software preloaded) that is associated with a particular hardware profile 825. For example, as depicted in FIG. 8, the hardware profile 825 may indicate a number of CPU cores (e.g., 40 CPU cores) and/or a number of memory units (e.g., 512 Gigabytes). It should be understood that any suitable features may represent (e.g., be associated with) a hardware profile, including, but not limited to, CPU resources, memory resources, data bus types, disk storage types, network card types, other processor types (e.g., GPU resource), etc. In some embodiments, the hardware profile of a physical computing device may be indicative of the device's ability to emulate a physical edge device (e.g., physical edge device 821), which may be associated with its own hardware profile (e.g., hardware profile 823). In some embodiments, emulation of physical edge device 821 by physical computing device 813A (e.g., provisioned as virtual edge device 815) may correspond to a reproduction of the hardware (and/or software) features of the physical edge device 821 by the virtual edge device 815. In some embodiments, the computer system 805 may select the particular physical computing device 813A based on confirming that the hardware profile 825 of the physical computing device 813A matches the hardware profile 823 of the physical edge device. For example, to be considered matching, the two hardware profiles may differ from one another by less than a threshold amount. The threshold amount may correspond to any suitable unit of measurement(s). For example, the various features of a hardware profile may be weighted together and/or individually assessed with a numeric score (e.g., included within a vector of scores). The vector representation for a given profile may be compared against another vector to determine a similarity between the vectors (e.g., a cosine similarity). It should be understood that any suitable method may be used to determine whether one device (e.g., a physical computing device that is a candidate for being provisioned as a virtual edge device) may serve as a sufficient emulator for another device (e.g., a physical edge device).

In some embodiments, a plurality of physical computing devices (e.g., a subset of the physical computing devices 813A-N) may selected for provisioning as a distributed computing cluster of virtual edge devices. In some embodiments, the distributed computing cluster may be used by a user to test performance of processing an increased number of workloads (and/or workflows) that is scaled up from what may be otherwise handled by a single virtual edge device. By testing performance and/or compatibility (e.g., an ability to be executed at a given edge device and/or cluster of edge devices) of processing workloads via a distributed computing cluster of virtual edge devices, embodiments herein may also enable users (e.g., customers) to determine how well a similarly configured distributed cluster of physical edge devices (e.g., connected together over a VPN) in a remote region would be able to handle similar amounts and/or types of workloads (e.g., based at least in part on throughput capacity, energy consumption, or the like).

In some embodiments, there may be a plurality of types of physical computing devices, each type having a particular hardware profile. For example, one hardware profile may include 40 CPU cores, while another profile may include 60 CPU cores. In some embodiments, there may also and/or alternatively be cluster types, for example, corresponding to a particular cluster configuration (e.g., a number of physical computing devices and/or types of devices for a particular cluster). In some embodiments, a customer may be provided with a user interface to be able to select what type of configuration they want to test with (e.g., via a virtual edge device) and/or eventually order for deployment (e.g., as a physical edge device).

In some embodiments, provisioning a physical computing device as a virtual edge device may include provisioning the physical computing device with one or more containers (e.g., Docker containers) that containerize a set of services. The set of services may be configured to execute subsequent customer workloads. For example, using FIG. 8 for illustration, suppose that user device 803 receives user input via a user interface. The user input requests the computer system 805 to provision a virtual edge device for the user, whereby the virtual edge device is provisioned to execute workloads for the user. In this example, suppose that the user already has at least cloud computing workloads 811A and 811B executing in the centralized cloud computing environment of public portion 830. The customer may want to determine, prior to placing an order for a physical edge device, how well these workloads would execute in an isolated environment (e.g., isolated portion 832), for example, a remote region of the world (e.g., isolated from the cloud). Accordingly, the customer requests provisioning of a virtual edge device to test (e.g., emulate) execution of these workloads prior to actual deployment in the remote region. The computer system 805 may the containerize at least workloads 811A and 811B into containers 817A and 817B, and then select a physical computing device to be provisioned as the virtual edge device. In this example, suppose that physical computing devices 813A-N are all bare metal devices of the same type, and device 813A is not already allocated for provisioning (e.g., it is available). Accordingly, the computer system 805 may select physical computing device 813A to be provisioned as the virtual edge device 815. The computer system 805 then may provision at least containers 817A and 817B to the virtual edge device 815. The computer system 805 may further provision a platform 819 (e.g., including an OS and/or core services), upon which the containers may be executed and/or otherwise operated upon.

It should be understood that any suitable number of workloads may be containerized into any suitable number of data containers. In some embodiments, the containerization process may be similar to as described herein (e.g., with reference to FIG. 1). For example, a containerization engine may be configured to provide OS-level virtualization to deliver software (e.g., services) in packages. In some embodiments, these data containers may be isolated from one another. In some embodiments, a data container may comprise any suitable type of data (and/or data types). For example, a data container may include a virtual machine. In some embodiments, a data container may include a block volume or an object storage unit (e.g., a package type). In some embodiments, a data container may include software, libraries, and/or configuration files. As described herein, the data container (and/or components of the data container) may be executable on a platform 819 (e.g., an OS) of the virtual edge device. The platform 819 may include one or more core services that are deployed with the OS, such that the platform 819 is able to execute (and/or load) the one or more containers.

Upon provisioning the virtual edge device 815 with the workloads, the computer system 805 may execute the workloads on the virtual edge device 815 and then provide results via the user interface to the user device 803. As described herein, the user interface may enable the user to determine a level of performance of the workloads on the virtual edge device 815. For example, the level of performance may indicate an efficiency of resource (e.g., memory, CPU, etc.) utilization when executing the workloads. This may also indicate whether one or more resources are bottlenecks, and/or whether more resources should be added and/or utilized (e.g., a distributed computing cluster) to assist with handling increased customer data input (e.g., images, videos, etc., uploaded by a customer agent). The customer may also be able to determine a level of compatibility of a workload (e.g., a degree to which the workload is executable at a physical edge device). For example, the results may indicate whether the same workload, which was executed as a cloud computing workload 111, also successfully executed when containerized on the virtual edge device 815. The level of performance and/or the level of compatibility that are indicated by the results may be indicative of similar metrics that measure execution of the workload on a physical edge device. In this manner, a user can assess performance of workload processing and/or perform end-to-end testing of workloads prior to actual deployment of a physical edge device (e.g., to a remote region, which may be resource intensive).

Figure 9:
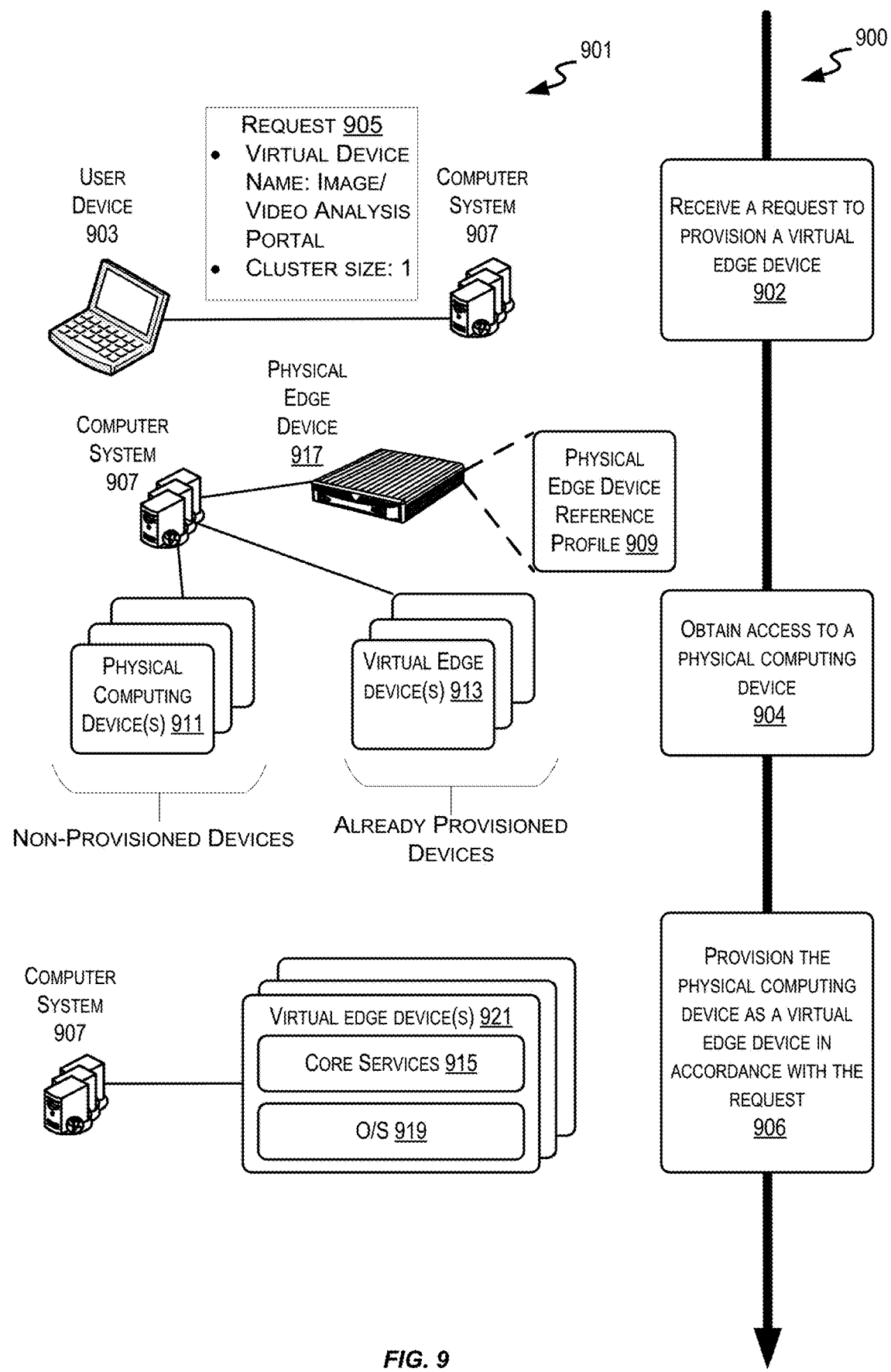
FIG. 9 is a simplified flow diagram illustrating an example technique for provisioning a virtual edge device, according to some embodiments.

FIG. 9 is a simplified flow diagram illustrating an example process 900 for provisioning a virtual edge device (virtual edge device 921, an example of the virtual edge device 815 of FIG. 8), according to some embodiments. Diagram 901 of FIG. 9 depicts example states that correspond to blocks of the process 900. The diagram 901 includes a user device 903 (e.g., similar to user device 803 of FIG. 8), computer system 907 (e.g., similar to computer system 805), one or more physical computing devices 911, one or more virtual edge devices 913, and at least one physical edge device 917. The physical computing devices 911 may be similar to one of the physical computing devices 813A-N that have not yet been provisioned as a virtual edge device (e.g., still a bare metal device), and/or was recently de-commissioned (e.g., image wiped to be restored as a bare metal device). Correspondingly, virtual edge device(s) 913 may individually be examples of the virtual edge device 815, which corresponds to a provisioned virtual edge device (e.g., provisioned with an OS, core services, etc.). In some embodiments, the computer system 907 may perform operations to execute the process 900. It should be understood that any suitable computing device may be suitable to perform process 900, and/or any of the other processes described herein.

Turning to process 900 in further detail, at block 902, a computer system receives a request to provision a virtual edge device. Using diagram 901 for further illustration, the computer system 907 may receive request 905 from the user device 903. For example, as depicted further herein with respect to FIGS. 12-14, the computer system 907 may provide a user interface for enabling the customer to submit request 905. In this example, the request 905 may indicate, among other elements, a virtual edge device name (e.g., "Image/Video Analysis Portal") and a cluster size (e.g., in this case, 1 device). In some embodiments, the requested cluster size may correspond to a plurality of physical computing devices that are requested to be provisioned as virtual edge devices (e.g., as a distributed computing cluster of virtual edge devices). In some embodiments, as described herein, there may be more than one type of physical edge device available for provisioning. Accordingly, there may be a plurality of types of physical computing devices that may be available for provisioning, respectively, as a virtual edge device (e.g., each type having a unique hardware profile that be determined to be a sufficient emulator for a corresponding physical edge device, with its own hardware profile). In this case, the request may indicate one or more types of physical computing devices that are requested to be provisioned as virtual edge devices. It should be understood that any suitable data may be indicated within a request, including, but not limited to, a customer account identifier, information about workload expectations, hardware requirements (e.g., storage, processing, compute, I/O requirements, etc.), networking requirements (e.g., VPN configuration settings), etc.

At block 904, the computer system obtains access to a physical computing device. For example, the computer system 907 may analyze the request 905 and determine that 1 device is requested for provisioning as a virtual edge device. In some embodiments, the computer system 907 may determine, from among the set of physical computing devices (e.g., in a lab environment), which are already provisioned (e.g., as virtual edge devices 913, and thus currently unavailable), and which are available for provisioning (e.g., physical computing devices 911). In some embodiments, the computer system 907 may analyze from among the non-provisioned physical computing devices 911 to select a suitable match for the request 905. This may include comparing a hardware profile of a candidate physical computing device 911 with a physical edge device reference profile 909 that identifies the hardware of a particular physical edge device 917. Upon determining that the hardware profiles are a suitable match (e.g., such that the physical computing device 911 may emulate the physical edge device 917), the computer system 907 may initiate a connection to the physical computing device 911. For example, the computer system 907 may connect to the physical computing device 911 over a suitable network path (e.g., using a MAC address, IP address, etc.). It should be understood that, although the physical computing device 911 may be accessible via the computer system 907, the device 911 may be separate (e.g., on a separate network) from other devices that are part of a centralized cloud computing environment.

At block 906, the computer system 907 provisions the selected physical computing device as a virtual edge device in accordance with the request. For example, continuing from block 904, the computer system 907 may image the selected physical computing device 911 with an OS 919 and one or more core services 915. For example, the core services may be associated with managing storage of objects, executing a container-orchestration system, executing a hypervisor on top of the OS 919, etc. The core services may enable any subsequently provisioned data containers (e.g., as described in reference to FIG. 10) to be successfully executed (and/or loaded) on (one or more of) the physical computing device 911. Upon imaging the device(s), the provisioning process for the new virtual edge device(s) 921 may be completed. In some embodiments, as described further in reference to FIGS. 15-17, the computer system 907 may provide a user interface to the user device 903 upon successfully provisioning the virtual edge device(s) 921. For example, the user interface may confirm the virtual device name, the status of one or more resources of the device, provide metrics information, enable a customer to control and/or otherwise manage the virtual edge device, etc.

Figure 10:
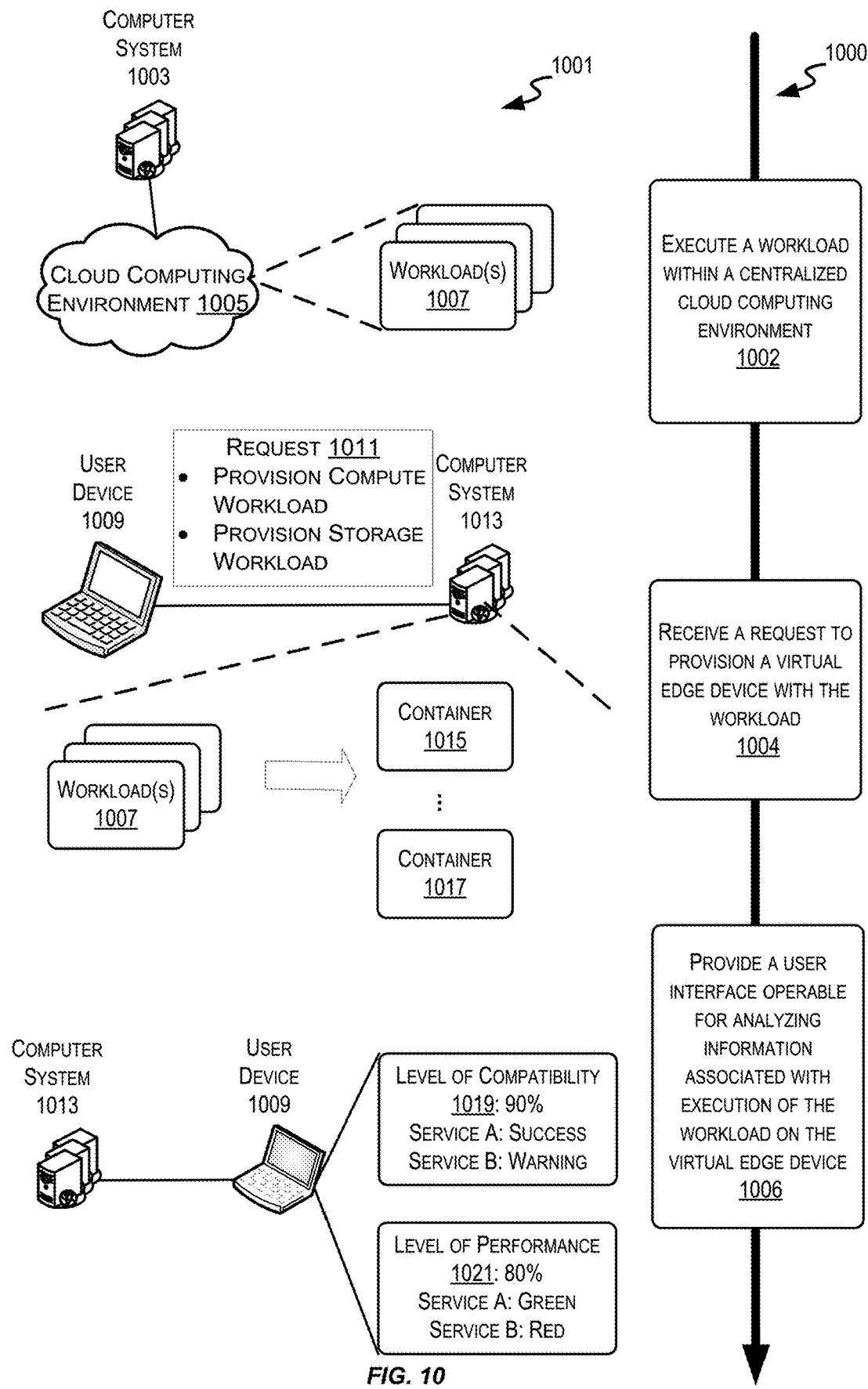
FIG. 10 is another simplified flow diagram illustrating an example technique for provisioning a workload to a virtual edge device for subsequent execution on the virtual edge device, according to some embodiments.

FIG. 10 is another simplified flow diagram illustrating an example process 1000 for provisioning a workload to a virtual edge device for subsequent execution on the virtual edge device, according to some embodiments. Diagram 1001 of FIG. 10 depicts example states that correspond to blocks of the process 1000. The diagram 1001 includes a user device 1009 (e.g., an example of the user device 903 of FIG. 9), computer system 1003 (e.g., an example of the computer system 907), and a cloud computing environment 1005 (e.g., an example of the cloud computing environment 807). As described herein, the cloud computing environment 1005 may include a plurality of devices, a portion of which may implement a centralized cloud computing environment that executes workloads in the cloud. Another portion of the cloud computing environment 1005 may partitioned (e.g., and/or otherwise separated, dedicate, isolate, or the like) from the centralized cloud computing environment, and may include physical computing devices suitable for provisioning as virtual edge devices.

Turning to process 1000 in further detail, at block 1002, a computer system may execute a workload(s) within a centralized cloud computing environment. Using diagram 1001 further illustration, the computer system 1003 may be connected (e.g., via a network, such as the Internet and/or a VPN) to the cloud computing environment 1005. One or more machines (e.g., a server cluster) may be tasked with executing workload(s) 1007 for the customer. For example, using an earlier illustration (e.g., the wildlife organization), a set of services may be configured to execute the workload(s) 1007. In the case of the wildlife organization, the services may include, for example, a machine learning model service (e.g., executing a "Compute Workload" that analyzes input images/videos) and a storage management service (e.g., executing a "Storage Workload" that stores analysis results in conjunction with the input images/videos). Other non-limiting examples of services that may execute workloads include a web server hosting service, a network management service, a database management service, an identity management service, and the like. In some embodiments, a service (and/or workload) may have a dependency on one or more other services (and/or workloads). For example, a workflow may involve executing workloads in a particular ordering, whereby the output of one workload may be used to trigger initiation of a subsequent workload (e.g., from the same or another service). It should be understood that any suitable set of services may be executed within the cloud computing environment 1005. Some of these services may be core services (e.g., storage management services, network management services) that natively run within the cloud computing environment 1005 (e.g., developed by the cloud services provider). Other services may be developed by a customer and deployed to the cloud. For example, the wildlife organization may train a machine learning classification model (e.g., using a neural network) to classify particular types of wildlife, and then deploy a service to the cloud 1005 that executes that model.

At block 1004, the computer system may receive a request to provision a virtual edge device with the workload(s). For example, the user device 1009 may transmit a request 1011 to the computer system 1013. In this example, the request 1011 may indicate that the customer wants to test the performance of one or more existing customer workloads 1007 (e.g., currently executing in the cloud 1005) on a virtual edge device (e.g., virtual edge device 911 of FIG. 9). As depicted in diagram 1001, request 1011 may indicate that at least two workloads (e.g., a "Compute Workload" and a "Storage Workload") are to be provisioned to the virtual edge device. Accordingly, the computer system 1013 may orchestrate (e.g., coordinate) the containerization of the workload(s) 1007 to be containerized as containers 1015, container 1017, etc. The containerization process may be performed similarly to as described herein, for example, via the containerization engine (e.g., Kubernetes). In some embodiments, the containerization process may involve generating a virtual machine that includes services to execute one or more workloads. In some embodiments, the containerization process may involve delivering software in packages in accordance with providing OS-level virtualization.

At block 1006, the computer system may provide a user interface that is operable for analyzing information associated with execution of the workload on the virtual edge device. For example, continuing from block 1004, the computer system 1013 may coordinate the deployment of the containers 1015, 1017, etc. to the virtual edge device. In this example, the provisioning of workloads (e.g., via containers) to the virtual edge device may be subsequent to the initial provisioning of the virtual edge device (e.g., at block 906 of FIG. 9). However, it should be understood that the provisioning of customer workloads may happen together (e.g., as part of the same process) with the provisioning of the underlying OS and/or core services. For example, as depicted further herein in FIG. 14, the customer can initially select both the initial virtual edge device parameters (e.g., a cluster size) as well as the workload(s) that are to be provisioned to the device. In some embodiments, the provisioning process may be structured in a particular order so as to ensure that OS and/or service dependencies are accounted for (e.g., such that pre-requisite services are installed first). In any case, upon completing the provisioning process that includes customer workloads, the computer system 1013 may instruct the virtual edge machine to execute the customer workloads. In some embodiments, the workloads may require user input (e.g., data uploaded from the user device 1009) to execute. In some embodiments, the workloads may be able to execute using existing data (e.g., downloaded from the cloud 1005). Upon executing the customer workloads/workflows, information associated with the results may be provided via the user interface by the computer system 1013 for presentation on user device 1009. In one example, the user interface may indicate a level of compatibility 1019. For example, the level of compatibility 1019 may indicate whether particular services (e.g., "Service A," Service B," etc., which execute customer workloads) perform similarly (e.g., in substantially the same manner, etc.) as they do in the cloud computing environment 1005 (e.g., where they were originally executing). For example, in one case, a workload, which was successfully executing in the cloud 1005, may fail to be performed successfully on the virtual edge device because one or more file types (e.g., executable in the cloud computing environment 1005) are not executable on the virtual edge device. This may be, for example, because the cloud computing device has a different software and/or hardware profile from the virtual edge device. Accordingly, the user interface may indicate, for each service, whether it executed successfully, or otherwise give a warning or error message if a failure is detected. In some embodiments, the level of compatibility 1019 may be associated with a number (e.g., 90%), which may cumulate compatibility results from multiple services. In some embodiments, one or more indicators (e.g., "health indicators") may be presented via the user interface, to indicate how well a workload is performing (e.g., color indicators, such as red, green, yellow, etc.) and/or is otherwise compatible with the cloud computing environment 1005. Any suitable health indicators may be presented (e.g., color coding, numerical statistics, etc.). Similarly, in this example, a level of performance 1021 may indicate how well Service A and Service B perform on the virtual edge device (e.g., the virtual edge device 815 of FIG. 8). In some embodiments, the level of performance 1021 may indicate, for example, resource utilization (e.g., what resources are being utilized), resource bottlenecks (e.g., resources with a latency metric that exceeds a predefined threshold), resource availability (e.g., what resources are available), etc. In some embodiments, the level of performance 1021 may indicate a similar degree of performance between executing a customer workload at a physical edge device and executing the customer workload at the virtual edge device. In this way, the user interface may indicate to the user how well a workload will perform on a physical edge device that may be eventually deployed (e.g., to a remote region). Similarly, the level of compatibility 1019 may indicate whether a workload that is executing in the centralized cloud computing environment 1005 is compatible with execution (e.g., can execute) at a physical edge device (e.g., based in part on a previous determination that the virtual edge device is a suitable emulator for the physical edge device according to respective hardware profiles).

Although the illustrations of FIGS. 9-10 are described primarily in reference to provisioning a single virtual edge device, it should be understood that similar techniques may be similarly used to provision a distributed computing cluster of virtual edge devices. In some embodiments, a distributed computing cluster of virtual edge devices may be configured similarly to that of a distributed computing cluster of physical edge devices (e.g., see FIG. 6). In this way, and, as described herein, a user can test scalability of workloads and/or workflows using an increased number of hardware resources. This may be useful to help a user more efficiently determine what type of configuration (e.g., an optimal cluster size) may be sufficient (e.g., capable of executing one or more workloads according to a predefined performance threshold) to deploy as a cluster of physical edge devices. In some embodiments, the computer system 1003 may enable a customer to request to add new virtual edge devices to an existing cluster of virtual edge devices. In some embodiments, the computer system 1003 may require a user to create a new cluster and then migrate workloads from a previous cluster to the new cluster.

Figure 15:
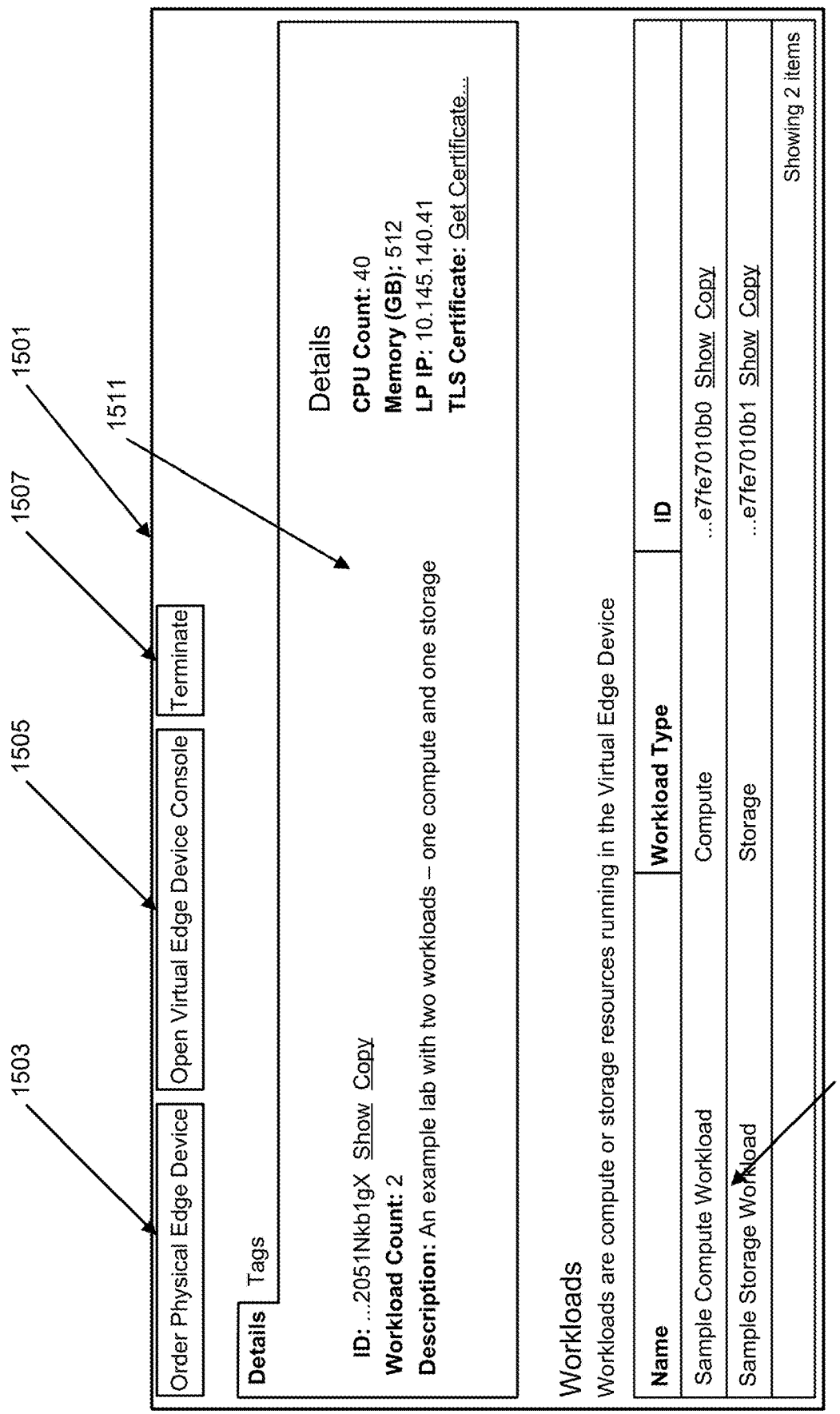
FIG. 15 illustrates another user interface utilizable for managing a virtual edge device, according to some embodiments.

In some embodiments, a user may run one or more iterations of workload executions to work out any performance and/or compatibility issues, to ensure that the workloads may execute. Upon completing the testing process, the user may determine that they are ready to order a deployment of physical edge devices that corresponds to the deployment of virtual edge devices. For example, as depicted in FIG. 15 and described further herein, the computer system 1003 may receive user input via a user interface to order one or more physical edge devices. The configuration for the one or more physical edge devices may be similar (e.g., the same or substantially the same) as that of the virtual edge device configuration (e.g., since the physical edge devices and virtual edge devices may have similar hardware profiles), thus enabling a more efficient deployment mechanism (as compared to deployment mechanisms that fail to utilize the techniques disclosed herein).

Furthermore, although the illustrations of FIGS. 9-10 are described primarily in reference to provisioning a virtual edge device within an existing workload from a centralized cloud computing environment, embodiments should not be construed to be so limited. For example, the computer system 1013 may enable a user to generate a new workload on a provisioned virtual edge device. In this example, the user interface receive user input to launch a new service, for example, executing a newly trained machine learning model (e.g., using a re-trained neural network). In some embodiments, the user interface may further enable the new service to be synchronized (e.g., uploaded) to the centralized cloud computing environment. It should be understood that any suitable synchronization of data (e.g., uploading from a virtual edge device to the centralized cloud computing environment (or vice versa), provisioning from the virtual edge device to a physical edge device, etc.) may be performed, according to embodiments herein.

Figure 11:
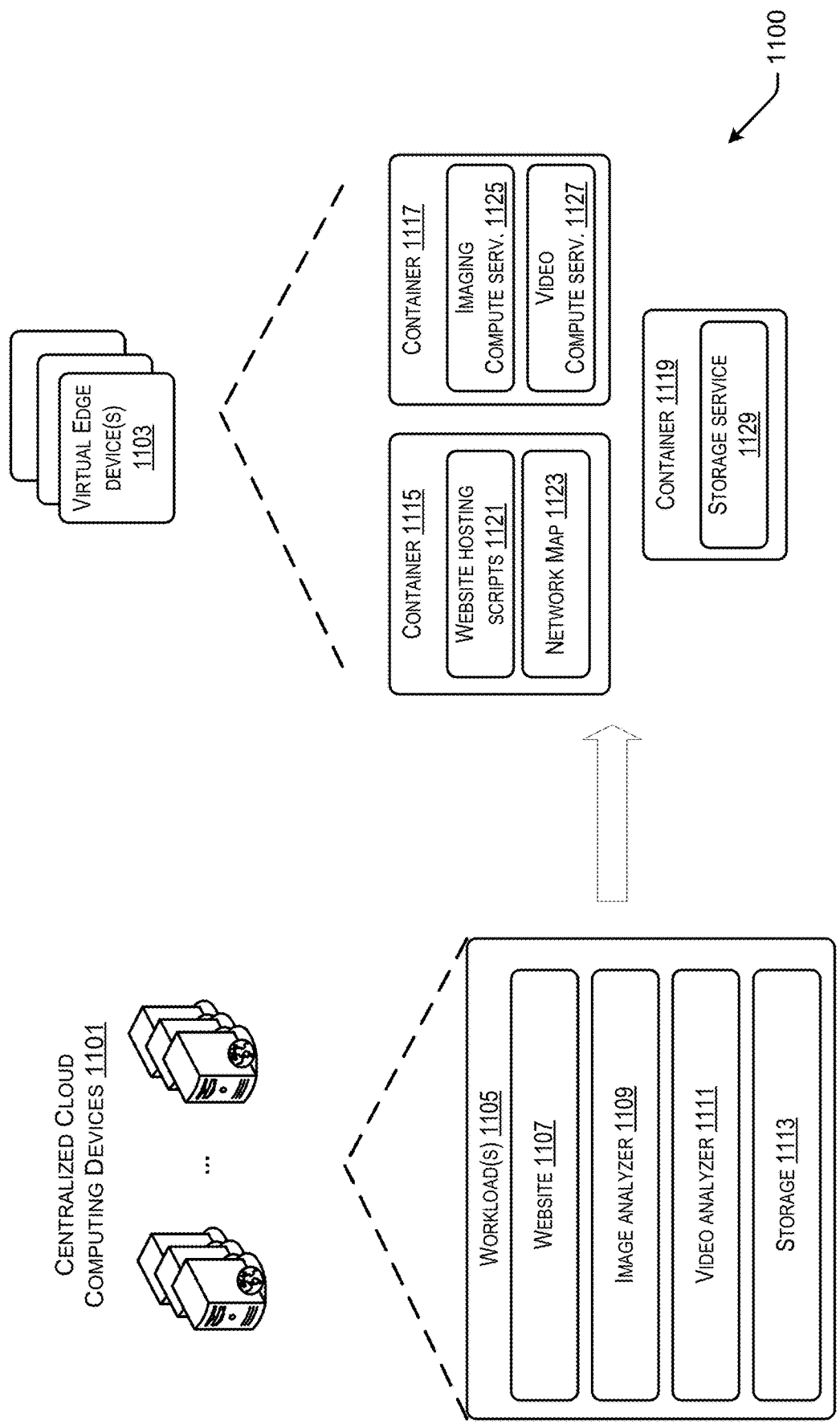
FIG. 11 is another simplified block diagram illustrating an example technique for containerizing a workload, executed in a centralized cloud environment, to be subsequently executed via a virtual edge device, according to some embodiments.

FIG. 11 is another simplified block diagram 1100 illustrating an example technique for containerizing a workload, executed in a centralized cloud environment, to be subsequently executed via a virtual edge device, according to some embodiments. FIG. 11 depicts centralized cloud computing devices 1101 of a centralized cloud computing environment. The centralized cloud computing devices 1101 may be dedicated for executing cloud computing workloads (e.g., cloud computing workloads 811 of FIG. 8). FIG. 11 further depicts one or more virtual edge devices 1103, which may be similar to other virtual edge devices described herein. By way of example, the virtual edge device(s) 1103 may individually be an example of the edge device 815 of FIG. 8.

Turning to FIG. 11 in further detail, the centralized cloud computing devices 1101 may collectively execute workload(s) 1105, which may be similar to workloads 1007 of FIG. 10. In this illustration, the workloads 1105 may include operating a web service that hosts website 1107, an image analyzer process 1109, a video analyzer process 1111, and a storage management process 1113. Any suitable workloads may be executed by the centralized cloud computing devices 1101. In some embodiments, the workloads 1105 may be executed by one or more services. In some embodiments, the workloads 1105 may be executed by any suitable number of devices of the centralized cloud computing devices 1101. For example, website 1107 may be hosted by one device, while a service that executes the image analyzer process 1109 may be hosted by another device. The devices may be in communication with each other using a suitable network protocol (e.g., via a VPN and/or public Internet channel).

As further depicted in FIG. 11, workloads 1105 may be containerized into one or more data containers (e.g., container 1115, container 1117, container 1119, etc.), which may be similar to containers 1015-1017 of FIG. 10. This containerization process may be performed at any suitable time and/or via any suitable mechanism. For example, a computer system (e.g., computer system 1003 of FIG. 10) may receive input to provision virtual edge device(s) 1103 with workloads 1105. The computer system 1003 may instruct a service in the centralized cloud computing environment to containerize the workloads 1007. The computer system 1003 may then provision (e.g., transfer and/or install) the containers to the virtual edge device(s) 1103. As described herein, a data container may utilize any suitable format and/or underlying platform. For example, a data container may include a virtual machine that is executed by a hypervisor. In another example, a data container may include a software package that executes via a container-orchestration system (e.g., Kubernetes). In the example of FIG. 11, container 1115 includes website hosting scripts 1121 and a network map 1123 (e.g., which may containerize the website 1107), container 1117 includes imaging compute service 1125 and video compute service 1127 (e.g., which may containerize image analyzer 1109 and video analyzer 1111), and container 1119 includes storage service 1129 (e.g., which may containerize storage management process 1113). It should be understood that workloads 1105 may be containerized and distributed across any suitable number of containers, and further the containers may be distributed across any suitable one or more virtual edge devices 1103 (e.g., across a plurality of virtual edge devices 1103, in the case of a distributed computing cluster of virtual edge devices). In some embodiments, the virtual edge devices 1103 (and/or one or more VM's executing on a particular virtual edge device) of a distributed computing cluster may be networked together via a VPN and/or utilizing one or more networking services, as described herein (e.g., in reference to FIGS. 5-6).

FIGS. 12-17 illustrate various user interfaces that may be associated with provisioning and/or managing a virtual edge device. As described herein, these user interfaces may be generated and provided by a computer system of a cloud services provider (e.g., computer system 805) for presentation on a user device (e.g., user device 803).

FIG. 12 illustrates a user interface utilizable for provisioning a virtual edge device, according to some embodiments. In FIG. 12, the user interface 1201 enables a user deice to create (e.g., provision) one or more virtual edge device(s) (e.g., similar to as described in reference to FIG. 9). For example, the user interface 1201 enables a user to set a device name, a password, a description, and/or select a cluster size 1203. As described herein, the cluster size 1203 may indicate a number of virtual edge devices that are requested to be provisioned (e.g., 1, 2, 10, 20, 40, etc.). In some embodiments, user interface 1201 may enable a user to select a particular type of virtual edge device (e.g., with a particular hardware profile).

Figure 13:
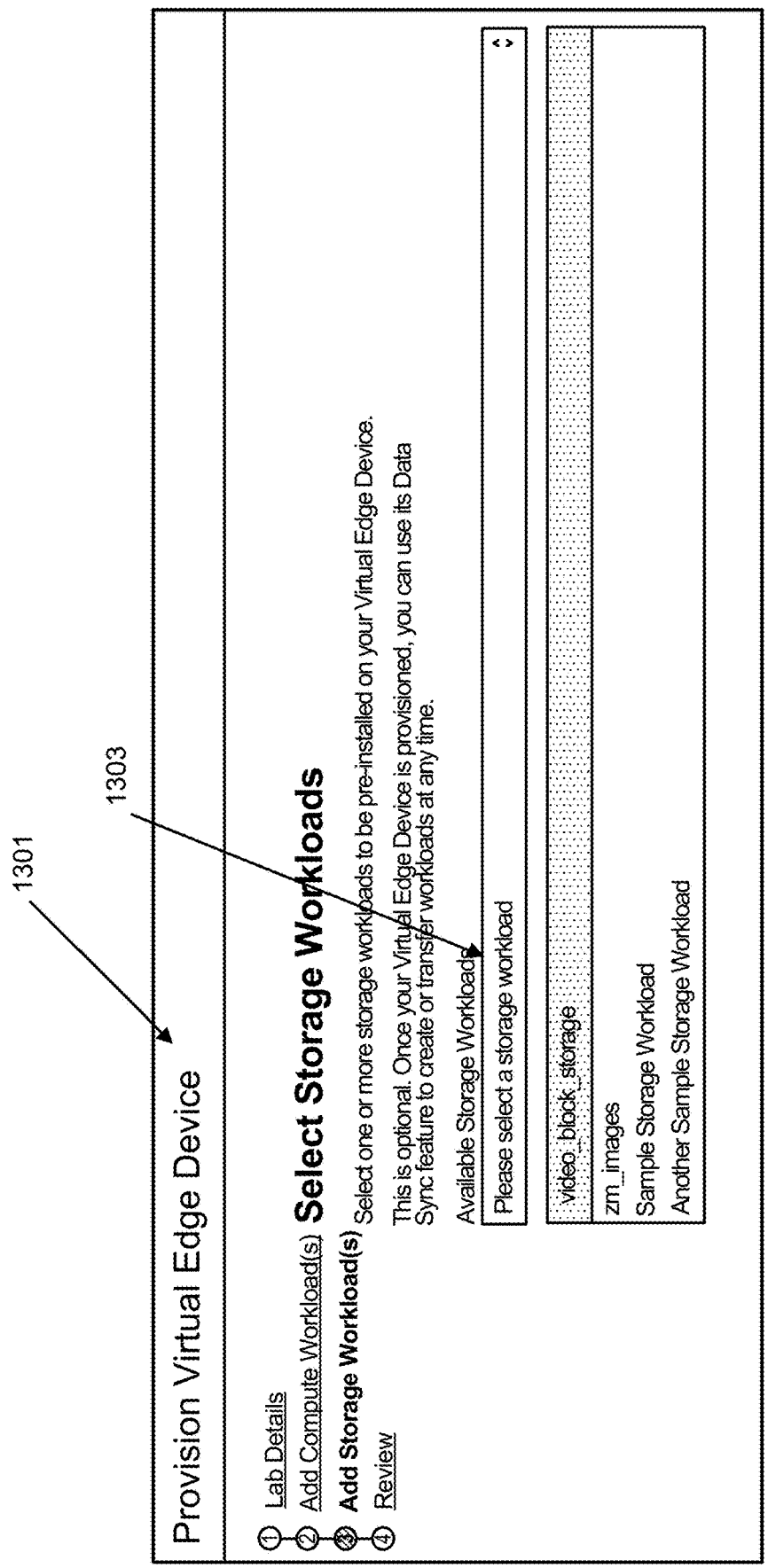
FIG. 13 illustrates another user interface utilizable for provisioning a virtual edge device, according to some embodiments.

FIG. 13 illustrates another user interface utilizable for provisioning a virtual edge device, according to some embodiments. The user interface 1301 may correspond to a next stage of the provisioning process, in this case, enabling a user to add one or more workloads (e.g., similar to as described in reference to FIG. 9). Note that, in this case, the user interfaces of FIGS. 12 and 13 enable a user to both provision (e.g., image) a new virtual edge device and provision one or more workloads (e.g., via containerization) within the same setup process (e.g., to initiate the performance of the processes 900 and 1000 of FIGS. 9 and 10). For example, in user interface 1301, the user may select a storage workload 1303 (e.g., which may already exist within the centralized cloud computing environment) to be transferred to the virtual edge device.

Figure 14:
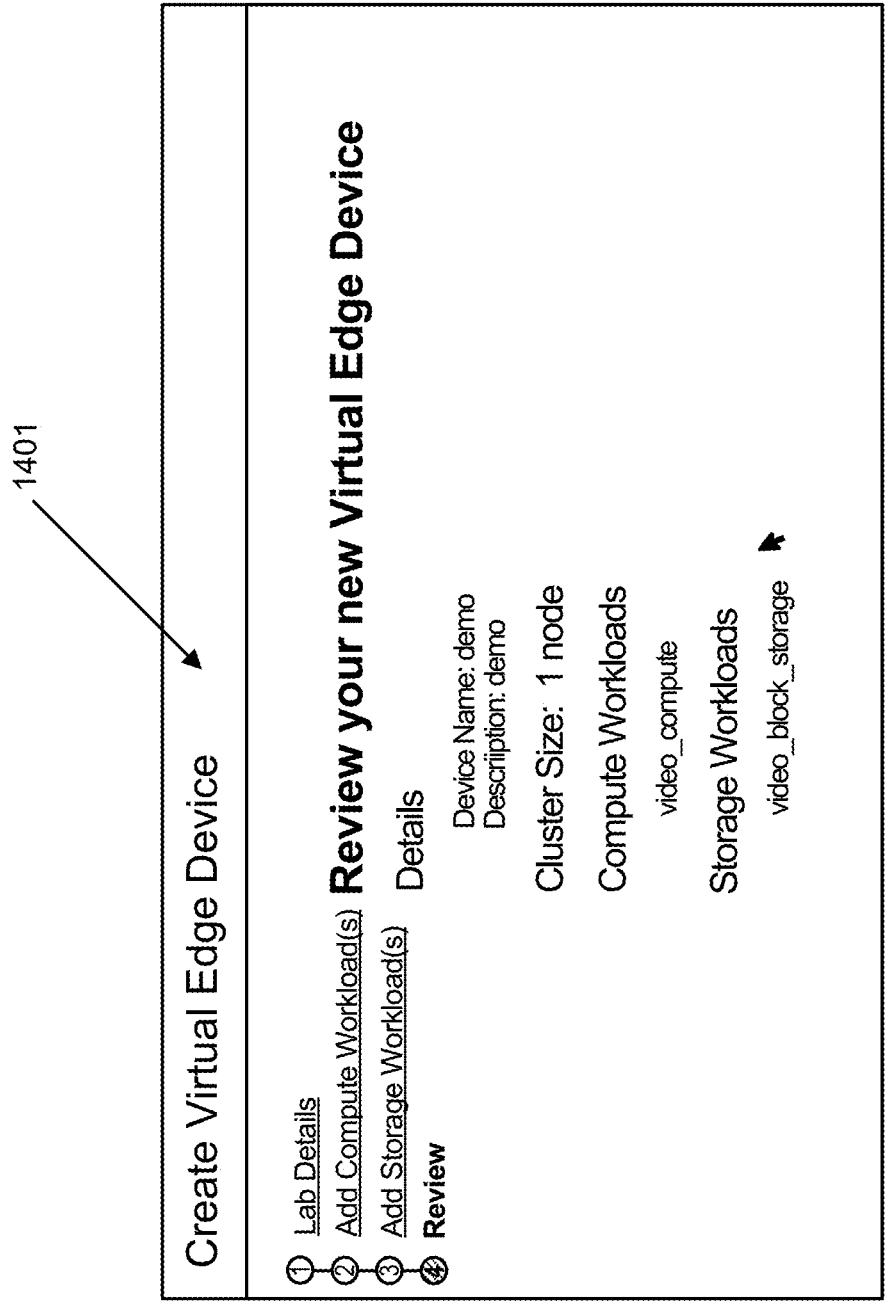
FIG. 14 illustrates another user interface utilizable for provisioning a virtual edge device, according to some embodiments.

FIG. 14 illustrates another user interface utilizable for provisioning a virtual edge device, according to some embodiments. The user interface 1401 shows a review page that summarizes details for the device that is requested to be provisioned as a virtual edge device. In this example, the customer has selected a compute workload (e.g., which may be associated with image analyzer 1109 and/or video analyzer 1111 of FIG. 11) and a storage workload (e.g., which may be associated with storage process 1113).

FIG. 15 illustrates another user interface 1501 utilizable for managing a virtual edge device, according to some embodiments. As depicted, user interface 1501 show details 1511 associated with a virtual edge device that was provisioned utilizing the user interfaces depicted via FIGS. 12-14. The details 1511 may include an identifier ("ID") for the virtual edge device, a workload count, a description of the workloads, hardware details (e.g., CPU count (e.g., 40 cores), memory (e.g., 512 GB), an IP address, a Transport Layer Security (TLS) certificate), etc.). In some embodiments, one or more of the hardware details may indicate a hardware profile of the virtual edge device. The user interface 1501 may also show details 1513 that summarize what workloads have been provisioned to the virtual edge device. The user interface 1501 may also enable the user to execute one or more tasks. For example, user interface element 1507 (e.g., a button) enables the user to terminate (e.g., de-commission) the provisioned virtual edge device(s) (e.g., restoring them to be available for re-provisioning). User interface element 1505 enables the user to open a virtual edge device console (e.g., for managing the virtual edge device, testing, generating, and/or configuring workloads), which may show a user interface similar to that depicted in FIG. 16. User interface element 1503 enables the user to order a physical edge device. For example, after the user verifies (e.g., via the virtual edge device console) the configuration of the virtual edge device, the user may order a physical edge device. This may include, for example, snapshotting an image of the virtual edge device and then imaging (e.g., provisioning with the snapshot image) the physical edge device. Accordingly, when the physical edge device(s) is activated (e.g., the configuration (e.g., of workloads, workflows, etc.) preferred by the user will already be pre-loaded and ready for immediate execution.

Figure 16:
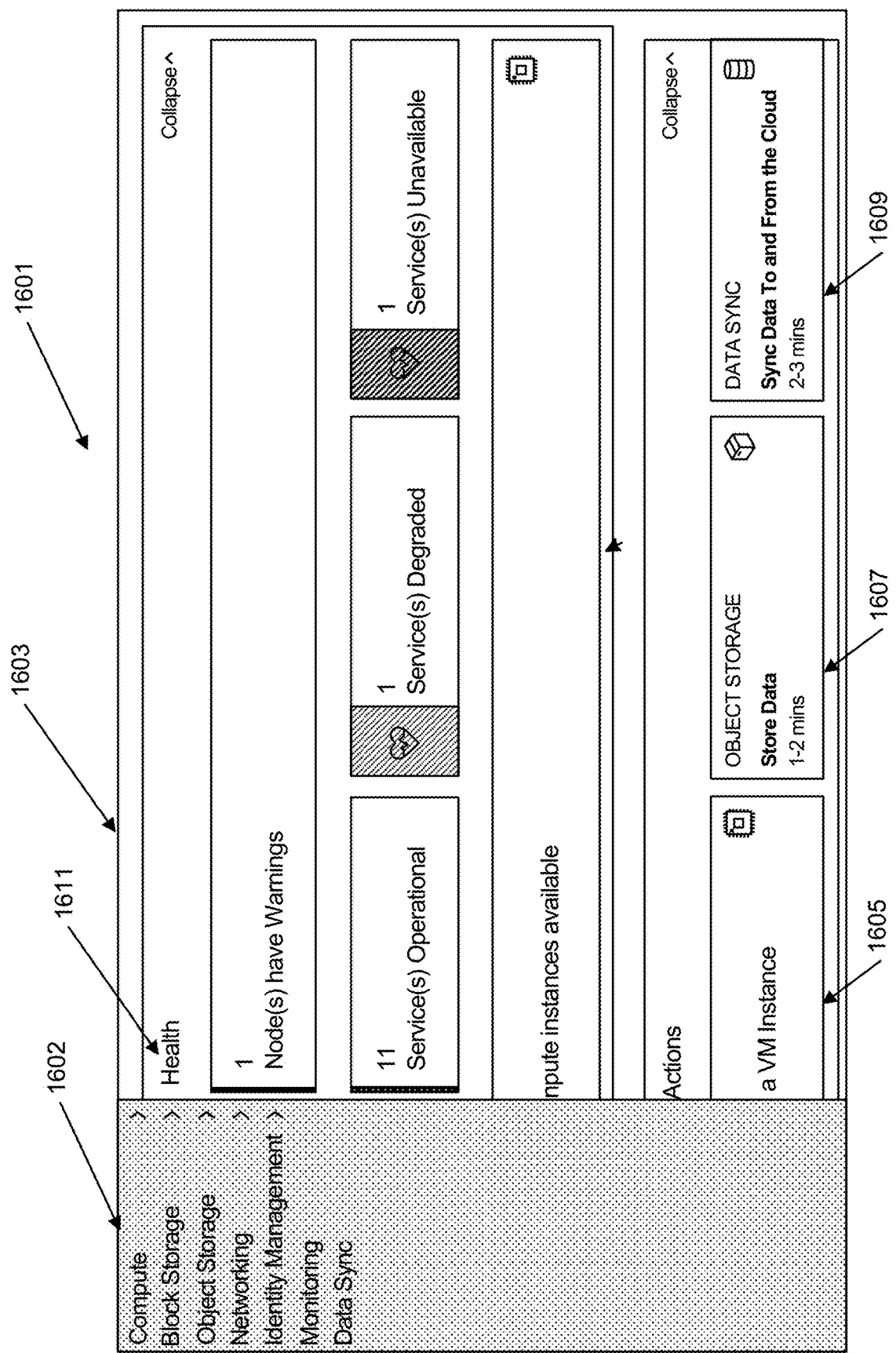
FIG. 16 illustrates another user interface utilizable for managing a virtual edge device, according to some embodiments.

FIG. 16 illustrates another user interface 1601 utilizable for managing a virtual edge device, according to some embodiments. The user interface 1601 may correspond to the virtual edge device console, described in reference to FIG. 15. In a right-side pane 1603 of user interface 1601, a summary of information associated with the virtual edge device may be displayed. This information may include health indicators, as described herein. For example, health indicators 1611 depict that one edge device (e.g., a node) has a warning (e.g., indicating a failure to process a particular data input), 11 services are operational, 1 service is degraded (e.g., whereby one or more features of the service are unavailable), and 1 service is unavailable. In some embodiments, health indicators indicate a degree of compatibility with execution of the same workloads in the centralized cloud computing environment. The right-side pane 1603 may also indicate, for example, workloads (e.g., compute instances) that are available for execution, and one or more actions that may be taken (e.g., launching a VM instance 1605, storing data 1607, and/or syncing data to/from the centralized cloud computing environment 1609). It should be understood that any suitable actions may be provided to manage the virtual edge device. The user interface 1601 may also provide (e.g., via a selectable menu elements 1602) one or more pages (e.g., sub-pages) that may provide more detailed information and/or features associated with managing a provisioned virtual edge device. For example, a "Compute" element may be selected from the selectable menu elements 1602 of the user interface 1601, whereby a page may be presented in the right-side pane 1603 to manage compute instances. Other non-limiting examples include a Block Storage element, Object Storage element, Network element, Identity Management element, a Monitoring element, and a Data Sync element.

Figure 17:
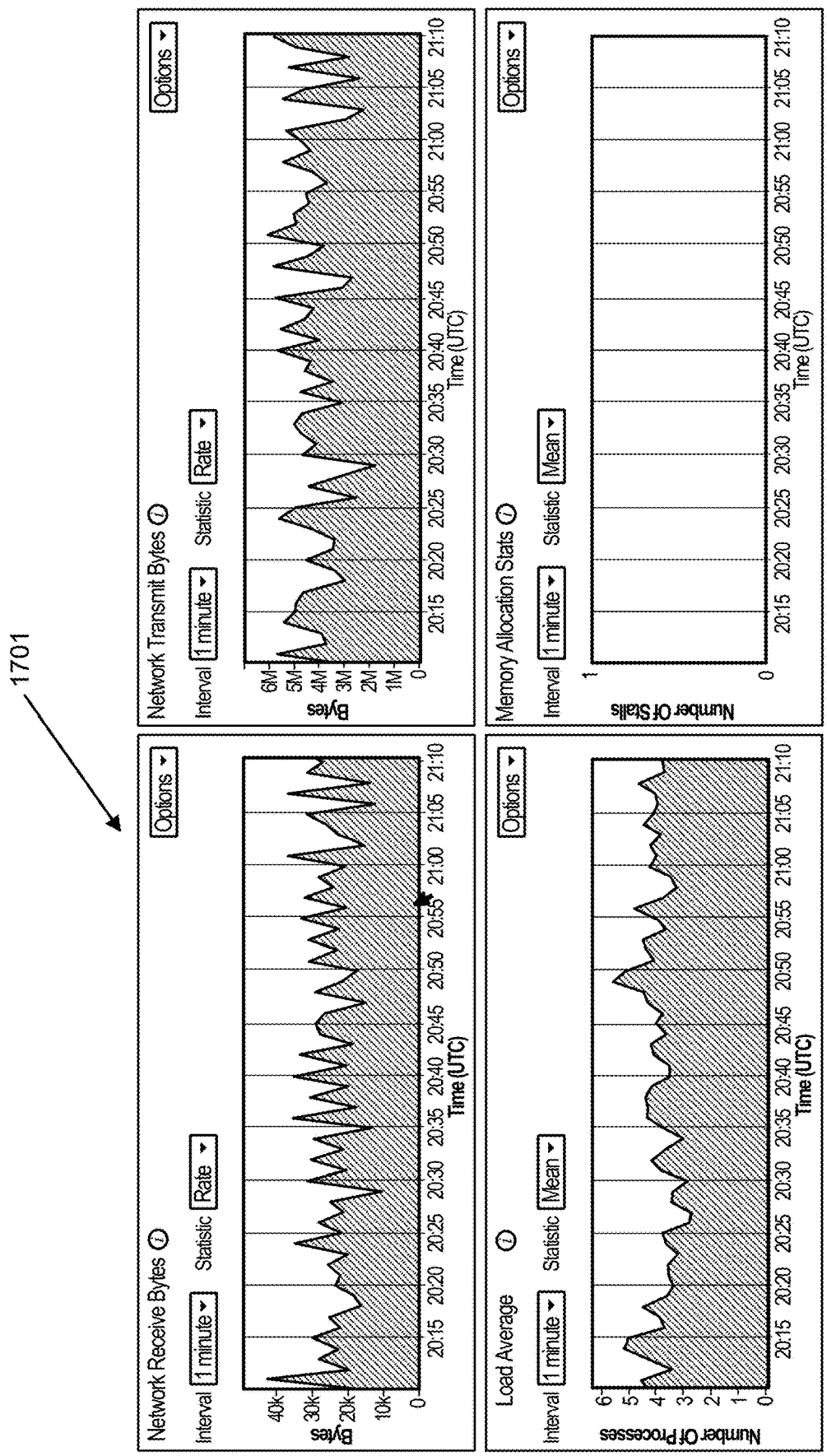
FIG. 17 illustrates another user interface utilizable for analyzing performance of a virtual edge device, according to some embodiments.

FIG. 17 illustrates another user interface 1701 utilizable for analyzing performance of a virtual edge device, according to some embodiments. In some embodiments, user interface 1701 may be accessible from another user interface (e.g., a virtual edge device console UI element 1505 of FIG. 15). User interface 1701 shows performance metrics, including, for example, a rate at which traffic is received (e.g., over a VPN), a rate at which traffic is transmitted, a load average (e.g., a number of processes executed over time), a memory allocation statistic, etc. It should be understood that any suitable performance metrics may be provided (e.g., processor utilization, memory utilization, disk utilization, bottleneck identification, etc.). As described herein, the performance metrics may be indicative of how the workloads may perform on a physical edge device, and thus, enable more efficient testing and configuration of the workloads.

Figure 18:
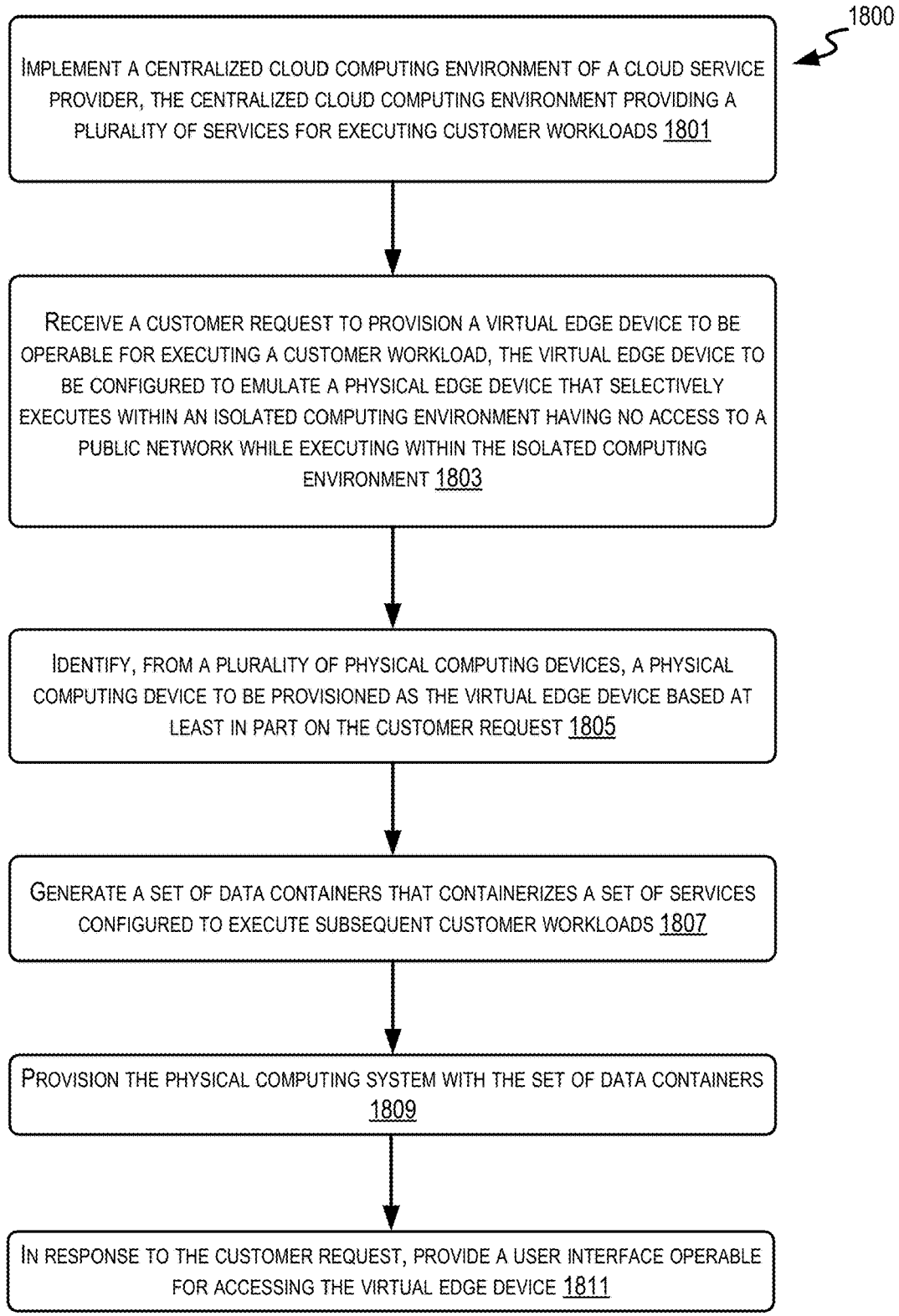
FIG. 18 illustrates a process for provisioning a workload to a virtual edge device for subsequent execution on the virtual edge device, according to some embodiments.

FIG. 18 illustrates a process 1800 for provisioning a workload to a virtual edge device for subsequent execution on the virtual edge device, according to some embodiments. In some embodiments, process 1800 of FIG. 18 may be performed by any suitable computer system described herein (e.g., computer system 805 of FIG. 1).

Process 1800 is respectively illustrated as a logical flow diagram, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

At block 1801, a computer system (e.g., computer system 805 of FIG. 8) may implement a centralized cloud computing environment of a cloud service provider (e.g., cloud computing environment 807 of FIG. 8). The centralized cloud computing environment may provide a plurality of services for executing customer workloads. In some embodiments, one or more operations of block 1801 may be similar to as described in reference to block 1002 of FIG. 10.

At block 1803, the computer system may receive a customer request (e.g., request 905 of FIG. 9) to provision a virtual edge device to be operable for executing a customer workload. The virtual edge device (e.g., the virtual edge device 815 of FIG. 8) may be configured to emulate a physical edge device that selectively executes within an isolated computing environment (e.g., a device having no access to a public network while executing within the isolated computing environment). In some embodiments, one or more operations of block 1803 may be similar to as described in reference to block 1004 of FIG. 10 and/or block 902 of FIG. 9. In some embodiments, the selective execution within the isolated environment may correspond to the customer selecting an operation mode for the physical edge device (e.g., in an isolated mode, or connected to the cloud).

At block 1805, the computer system may identify, from a plurality of physical computing devices (e.g., physical computer device(s) 911 of FIG. 9), a physical computing device to be provisioned as the virtual edge device based at least in part on the customer request. In some embodiments, one or more operations of block 1805 may be similar to as described in reference to block 904 of FIG. 9. For example, the physical computing device may have a first hardware profile that differs from a second hardware profile of the physical edge device by less than a threshold amount. In some embodiments, the threshold amount indicates at least one of: (I) a similar degree of performance between executing a customer workload at the physical edge device and executing the customer workload at the virtual edge device or (II) whether a customer workload that is executing in the centralized cloud computing environment is compatible with execution (e.g., able to be executed) at an edge device. In some embodiments, the physical computing device is a bare metal device dedicated to a single customer. In some embodiments, the customer request may request to provision a plurality of devices as a distributed computing cluster of virtual edge devices. In this case, the virtual edge device may be one of a plurality of virtual edge devices that are identified and obtained.

At block 1807, the computer system may generate a set of data containers (e.g., Docker containers, etc.) that containerizes a set of services configured to execute subsequent customer workloads. In some embodiments, one or more operations of block 1807 may be similar to as described in reference to block 1004 of FIG. 10 and/or FIG. 11.

At block 1809, the computer system may provision the physical computing device with the set of data containers (e.g., Docker containers, etc.). In some embodiments, one or more operations of block 1809 may be similar to as described in reference to block 1006 and/or FIG. 11.

At block 1811, the computer system may, in response to the customer request, provide a user interface operable for accessing the virtual edge device. In some embodiments, one or more operations of block 1811 may be similar to as described in reference to block 1006 of FIG. 10 and/or one of the interfaces depicted in reference to FIGS. 12-17. In some embodiments, the user interface may be operable for execution one or more subsequent operations on behalf of the customer. For example, the computer system may receive, via the user interface, a request to execute a workload of subsequent customer workloads associated with the set of services previously provisioned. The computer system may then execute, at the physical computing device that was provisioned as the virtual edge device, the workload utilizing at least one of the set of services in accordance with the request, whereby executing the workload at the provisioned virtual edge device emulates executing the workload at the physical edge device. In another example, the computer system may receive, via the user interface, a request to generate a new workflow via the virtual edge device. The virtual edge device may generate the new workflow. In some embodiments, in response to a second request via the user interface, the computer system may facilitate exporting the new workflow to the physical edge device that was emulated by the virtual edge device.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or modules are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A computer-implemented method, comprising:
   implementing a centralized cloud computing environment of a cloud service provider, the centralized cloud computing environment providing a plurality of services for executing customer workloads;
   receiving, by a computer system of the cloud service provider, a customer request to provision a virtual edge device to be operable for executing a customer workload, the virtual edge device to be configured to emulate a physical edge device that selectively executes within an isolated computing environment having no access to a public network while executing within the isolated computing environment;
   identifying, by the computer system from a plurality of physical computing devices, a physical computing device to be provisioned as the virtual edge device based at least in part on the customer request;
   generating, by the computer system, a set of data containers that containerizes a set of services configured to execute subsequent customer workloads;
   provisioning, by the computer system, the physical computing device with the set of data containers; and
   in response to the customer request, providing, by the computer system, a user interface operable for accessing the virtual edge device.

2. The computer-implemented method of claim 1, wherein the virtual edge device has a first hardware profile that differs from a second hardware profile of the physical edge device by less than a threshold amount.

3. The computer-implemented method of claim 2, wherein the user interface indicates at least one of: (I) a performance metric associated with executing the customer workload at the virtual edge device or (II) whether the customer workload that is executing in the centralized cloud computing environment is compatible with execution at an edge device.

4. The computer-implemented method of claim 1, further comprising:
   receiving, via the user interface, a request to execute a workload of the subsequent customer workloads associated with the set of services; and
   executing, at the physical computing device that was provisioned as the virtual edge device, the workload utilizing at least one of the set of services in accordance with the request, wherein executing the workload at the provisioned virtual edge device emulates executing the workload at the physical edge device.

5. The computer-implemented method of claim 1, wherein the virtual edge device is one of a plurality of virtual edge devices configured to operate as a distributed computing cluster, and wherein the method further comprises:
   receiving, via the user interface, a request to execute a workload; and
   executing, by the distributed computing cluster, one or more operations corresponding to the workload.

6. The computer-implemented method of claim 1, wherein the physical computing device is a bare metal device dedicated to a single customer.

7. The computer-implemented method of claim 1, further comprising:
   receiving, via the user interface, a request to generate a new workflow via the virtual edge device;
   generating the new workflow; and
   in response to a second request via the user interface, exporting the new workflow to the physical edge device that was emulated by the virtual edge device.

8. A computer system of a cloud service provider, comprising:
   a memory comprising computer-executable instructions; and
   one or more processors in communication with the memory and configured to access the memory and execute the computer-executable instructions to:
   implement a centralized cloud computing environment of the cloud service provider, the centralized cloud computing environment providing a plurality of services for executing customer workloads;
   receive a customer request to provision a virtual edge device to be operable for executing a customer workload, the virtual edge device to be configured to emulate a physical edge device that selectively executes within an isolated computing environment having no access to a public network while executing within the isolated computing environment;
   identify, from a plurality of physical computing devices, a physical computing device to be provisioned as the virtual edge device based at least in part on the customer request;

generate a set of data containers that containerizes a set of services configured to execute subsequent customer workloads;

provision the physical computing device with the set of data containers; and in response to the customer request, provide a user interface operable for accessing the virtual edge device.

9. The computer system of claim 8, wherein the virtual edge device has a first hardware profile that differs from a second hardware profile of the physical edge device by less than a threshold amount.

10. The computer system of claim 9, wherein the user interface indicates at least one of: (I) a performance metric associated with executing the customer workload at the virtual edge device or (II) whether the customer workload that is executing in the centralized cloud computing environment is compatible with execution at an edge device.

11. The computer system of claim 8, wherein the instructions further comprise:

receiving, via the user interface, a request to execute a workload of the subsequent customer workloads associated with the set of services; and executing, at the physical computing device that was provisioned as the virtual edge device, the workload utilizing at least one of the set of services in accordance with the request, wherein executing the workload at the provisioned virtual edge device emulates executing the workload at the physical edge device.

12. The computer system of claim 8, wherein the virtual edge device is one of a plurality of virtual edge devices configured to operate as a distributed computing cluster, and wherein the instructions further comprise:

receiving, via the user interface, a request to execute a workload; and executing, by the distributed computing cluster, one or more operations corresponding to the workload.

13. The computer system of claim 8, wherein the physical computing device is a bare metal device dedicated to a single customer.

14. The computer system of claim 8, wherein the instructions further comprise:

receiving, via the user interface, a request to generate a new workflow via the virtual edge device;

generating the new workflow; and in response to a second request via the user interface, exporting the new workflow to the physical edge device that was emulated by the virtual edge device.

15. One or more non-transitory computer-readable storage media comprising computer-executable instructions that, when executed by one or more processors of a cloud service provider, cause the one or more processors to:

implement a centralized cloud computing environment of the cloud service provider, the centralized cloud computing environment providing a plurality of services for executing customer workloads;

receive a customer request to provision a virtual edge device to be operable for executing a customer workload, the virtual edge device to be configured to emulate a physical edge device that selectively executes within an isolated computing environment having no access to a public network while executing within the isolated computing environment;

identify, from a plurality of physical computing devices, a physical computing device to be provisioned as the virtual edge device based at least in part on the customer request;

generate a set of data containers that containerizes a set of services configured to execute subsequent customer workloads;

provision the physical computing device with the set of data containers; and in response to the customer request, provide a user interface operable for accessing the virtual edge device.

16. The one or more non-transitory computer-readable storage media of claim 15, wherein the virtual edge device has a first hardware profile that differs from a second hardware profile of the physical edge device by less than a threshold amount.

17. The one or more non-transitory computer-readable storage media of claim 16, wherein the user interface indicates at least one of: (I) a performance metric associated with executing the customer workload at the virtual edge device or (II) whether the customer workload that is executing in the centralized cloud computing environment is compatible with execution at an edge device.

18. The one or more non-transitory computer-readable storage media of claim 15, wherein the instructions further comprise:

receiving, via the user interface, a request to execute a workload of the subsequent customer workloads associated with the set of services; and executing, at the physical computing device that was provisioned as the virtual edge device, the workload utilizing at least one of the set of services in accordance with the request, wherein executing the workload at the provisioned virtual edge device emulates executing the workload at the physical edge device.

19. The one or more non-transitory computer-readable storage media of claim 15, wherein the virtual edge device is one of a plurality of virtual edge devices configured to operate as a distributed computing cluster, and wherein the instructions further comprise:

receiving, via the user interface, a request to execute a workload; and executing, by the distributed computing cluster, one or more operations corresponding to the workload.

20. The one or more non-transitory computer-readable storage media of claim 15, wherein the instructions further comprise:

receiving, via the user interface, a request to generate a new workflow via the virtual edge device;

generating the new workflow; and in response to a second request via the user interface, exporting the new workflow to the physical edge device that was emulated by the virtual edge device, the physical computing device corresponding to a bare metal device that is dedicated to a single customer.

\* \* \* \* \*